(12) United States Patent
Karasawa

(10) Patent No.: US 10,926,040 B2
(45) Date of Patent: Feb. 23, 2021

(54) SYRINGE PROTECTING DEVICE

(71) Applicant: Forte Grow Medical Co., Ltd., Sano (JP)

(72) Inventor: Koji Karasawa, Sano (JP)

(73) Assignee: FORTE GROW MEDICAL Co., Ltd., Sano (JP)

( * ) Notice: Subject to any disclaimer, the term of this patent is extended or adjusted under 35 U.S.C. 154(b) by 316 days.

(21) Appl. No.: 16/063,131

(22) PCT Filed: Sep. 14, 2016

(86) PCT No.: PCT/JP2016/077147
§ 371 (c)(1),
(2) Date: Jun. 15, 2018

(87) PCT Pub. No.: WO2017/104196
PCT Pub. Date: Jun. 22, 2017

(65) Prior Publication Data
US 2018/0369500 A1 Dec. 27, 2018

(30) Foreign Application Priority Data
Dec. 18, 2015 (JP) .............................. JP2015-247707

(51) Int. Cl.
*A61M 5/32* (2006.01)

(52) U.S. Cl.
CPC ............ *A61M 5/3245* (2013.01); *A61M 5/32* (2013.01); *A61M 5/329* (2013.01); *A61M 5/3271* (2013.01); *A61M 2005/325* (2013.01)

(58) Field of Classification Search
CPC ...... A61M 5/32; A61M 5/3245; A61M 5/329; A61M 5/3269; A61M 5/3271; A61M 5/3272; A61M 2005/325
See application file for complete search history.

(56) References Cited

U.S. PATENT DOCUMENTS

| | | | |
|---|---|---|---|
| 4,923,446 A | 5/1990 | Page et al. | |
| 4,998,924 A | 3/1991 | Ranford | |

(Continued)

FOREIGN PATENT DOCUMENTS

| | | |
|---|---|---|
| CN | 103957971 A | 7/2014 |
| EP | 2 578 256 A1 | 4/2013 |

(Continued)

OTHER PUBLICATIONS

Extended European Search Report issued in counterpart European Application No. 16875182.4 dated Aug. 14, 2019 (five (5) pages).

(Continued)

*Primary Examiner* — Manuel A Mendez
*Assistant Examiner* — Justin L Zamory
(74) *Attorney, Agent, or Firm* — Crowell & Moring LLP

(57) ABSTRACT

A syringe protecting device equipped with an outer cylinder, an inner cylinder and a spring, wherein, when the spring is released from its compressed state, the inner cylinder is moved rearward with respect to the outer cylinder so that a syringe needle is stored inside the outer cylinder, and the syringe protecting device further equipped with a releasable pre-locking mechanism for fixing the inner cylinder to the outer cylinder while maintaining the spring in the compressed state in the front-rear direction, wherein, the pre-locking mechanism fixes the inner cylinder before movement to the outer cylinder by engaging the protruding sections of the ring with the engaging sections of the through groove sections.

13 Claims, 25 Drawing Sheets

(56) References Cited

U.S. PATENT DOCUMENTS

| | | | |
|---|---|---|---|
| 5,201,708 | A | 4/1993 | Martin |
| 5,318,538 | A | 6/1994 | Martin |
| 6,319,233 | B1 | 11/2001 | Jansen et al. |
| 2002/0004649 | A1 | 1/2002 | Jansen et al. |
| 2005/0010136 | A1 | 1/2005 | Restelli et al. |
| 2005/0085776 | A1 | 4/2005 | Hommann et al. |
| 2007/0078382 | A1 | 4/2007 | Hommann et al. |
| 2013/0296798 | A1 | 11/2013 | Roberts et al. |
| 2014/0039406 | A1 | 2/2014 | Verespej et al. |
| 2014/0107577 | A1* | 4/2014 | Boyd .................. A61M 5/3213 604/111 |
| 2014/0243760 | A1 | 8/2014 | Slemmen et al. |
| 2014/0249481 | A1 | 9/2014 | Slemmen et al. |

FOREIGN PATENT DOCUMENTS

| | | | |
|---|---|---|---|
| JP | 2005-519647 | A | 7/2005 |
| JP | 2007-521845 | A | 8/2007 |
| JP | 2014-503301 | A | 2/2014 |
| JP | 2014-528303 | A | 10/2014 |
| JP | 2014-528304 | A | 10/2014 |
| JP | 2015-514518 | A | 5/2015 |
| WO | WO 2012/093071 | A1 | 7/2012 |

OTHER PUBLICATIONS

Cover page of EP 2 661 299 A0 published Nov. 13, 2013 (one (1) page).
International Search Report (PCT/ISA/210) issued in PCT Application No. PCT/JP2016/077147 dated Oct. 18, 2016 with English translation (four (4) pages).
Japanese-language Written Opinion (PCT/ISA/237) issued in PCT Application No. PCT/JP2016/077147 dated Oct. 18, 2016 (three (3) pages).

* cited by examiner

FRONT ←

SYRINGE PROTECTING DEVICE

CROSS-REFERENCE TO RELATED APPLICATIONS

This application is a 371 national phase entry of PCT/JP2016/077147, filed Sep. 14, 2016, which claims priority to Japanese application 2015-247707, filed Dec. 18, 2015, the disclosures of both of which are expressly incorporated by reference herein.

TECHNICAL FIELD

The present invention relates to a syringe protecting device, for example, for safely storing, using and discarding a prefilled syringe, so that needle sticking accidents do not occur, more particularly, to a syringe protecting device capable of storing a syringe needle inside the device itself after the administration of a medical solution.

BACKGROUND ART

With respect to prefilled syringes, various kinds of protecting devices have been proposed conventionally to prevent needle sticking accidents. In particular, in the case that a prefilled syringe is used for a therapeutic medical solution for an infectious disease mediated by blood, a needle sticking accident after the administration of the medical solution will become a serious accident. Hence, such a protecting device is indispensable.

PRIOR ART DOCUMENT

Patent Document

Patent Document 1: JP 2005-519647 A
Patent Document 2: JP 2015-514518 A
Patent Document 3: US 2014/0107577 A1
Patent Document 4: U.S. Pat. No. 5,201,708 A
Patent Document 5: U.S. Pat. No. 5,318,538 A
Patent Document 6: US 2002/0004649 A1

SUMMARY OF INVENTION

Technical Problem

However, such conventional protecting devices have the following problems.

(1) Although a locking mechanism is provided in some cases to avoid operation of such a conventional protecting device before use, the locking mechanism is unreliable. Hence, there is a danger that operation may occur when the protecting device is transported or stored, or when a prefilled syringe is set to the protecting device, or when a prefilled syringe having been set to the protecting device is transported, stored or used for the administration of a medical solution, that is, when the protecting device is not intended to operate. In other words, there is a danger that the conventional protecting device may malfunction.

(2) Although a locking mechanism is provided in some cases to avoid the exposure of a syringe needle having been stored after use, the locking mechanism is unreliable. Hence, there is a danger that the syringe needle may be exposed and a needle sticking accident may occur, for example, when such a conventional syringe protecting device is discarded.

(3) Such a conventional protecting device is complicated in structure.

(4) Such a conventional protecting device has a large number of components.

(5) Such a conventional protecting device causes trouble in assembling.

(6) Such a conventional protecting device causes difficulty in visually recognizing the state of a medical solution being administered.

A main object of the present invention is to provide a syringe protecting device capable of preventing malfunction more securely by using a simple configuration.

Solution to Problem

The present invention provides a syringe protecting device, when mounted on a syringe and used, operating so as to store a syringe needle after the administration of a medical solution, comprising:
an outer cylinder having a front end opening and a rear end opening,
an inner cylinder, having a front end opening and a rear end opening and inserted into the outer cylinder, to which the syringe can be inserted and fixed, and
a spring provided in the circumferential space between the inner face of the rear section of the outer cylinder and the outer face of the rear section of the inner cylinder in a compressed state in the front-rear direction so that the inner cylinder is energized rearward with respect to the outer cylinder, wherein
when the spring is released from the compressed state, the inner cylinder is moved rearward with respect to the outer cylinder so that the syringe needle is stored inside the outer cylinder,
the syringe protecting device further comprising:
a releasable pre-locking mechanism for fixing the inner cylinder to the outer cylinder while maintaining the spring in a compressed state in the front-rear direction, wherein
the pre-locking mechanism comprises:
a ring, different from the inner cylinder and the outer cylinder, being fitted on the rear section of the inner cylinder so as to be slidable in the circumferential direction and so as not to be movable in the front-rear direction, and
through groove sections formed in the rear section of the outer cylinder, wherein
the ring has one or more outward protruding sections in the circumferential direction,
the protruding sections are engaged with the engaging sections of the through groove sections, and
the through groove section comprises a straight section being open at the rear end edge thereof and extended in the front-rear direction, an inclined section extended obliquely rearward from the front end of the straight section, and the engaging section extended rearward linearly from the rear end of the inclined section, wherein
in the case that the inner cylinder is pressed so as to further compress the spring, the ring is rotated in the circumferential direction with respect to the inner cylinder and the outer cylinder, the protruding sections come out from the engaging sections, pass through the inclined sections and enter the straight sections, whereby the pre-locking mechanism is released, and
when the pre-locking mechanism is released, the inner cylinder is moved rearward with respect to the outer cylinder by the spring by the distance along which the syringe needle is moved and stored in the outer cylinder.

Advantageous Effects of Invention

With the syringe protecting device according to the present invention, since the syringe needle can be stored inside the outer cylinder after the use of the syringe, needle sticking accidents can be prevented, and the following advantages can be obtained.

(a) With the pre-locking mechanism, since the protruding sections of the ring can be firmly held by the engaging sections of the through groove sections, the inner cylinder before use can be firmly fixed to the outer cylinder, whereby malfunction can be prevented.

(b) Furthermore, with the post-locking mechanism, since the protruding sections of the tongue sections can be firmly held by the engaging sections of the slide groove sections, the inner cylinder having been operated can be firmly fixed to the outer cylinder; hence, the syringe needle can be prevented from being exposed, for example, when the protecting device is stored or discard after the operation of the protecting device, whereby needle sticking accidents can be prevented.

DESCRIPTION OF EMBODIMENTS

A syringe protecting device according to an embodiment of the present invention will be described below referring to the accompanying drawings.

[Configuration]

Figure 1:
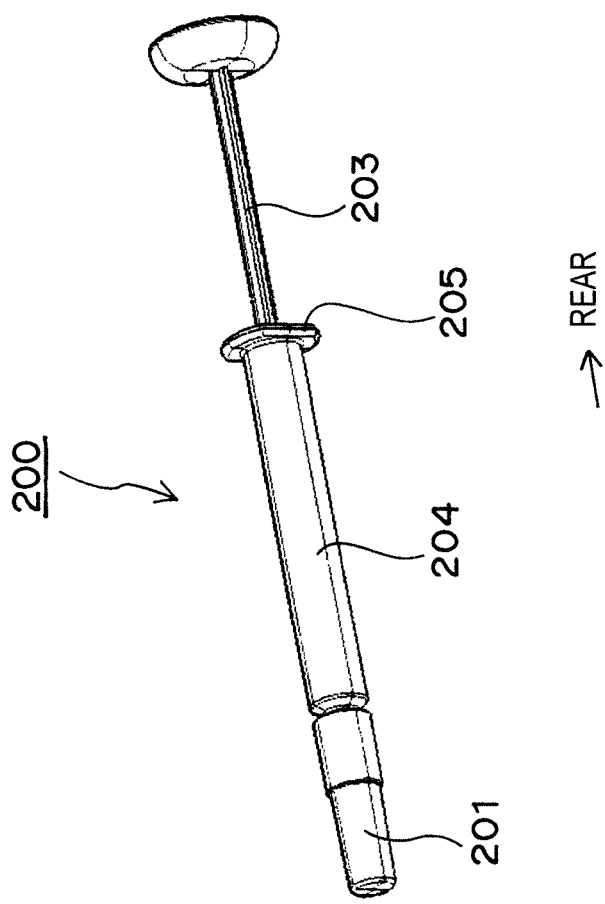
FIG. 1 is a perspective view showing a state in which a syringe protecting device according to an embodiment is just before being mounted on a syringe.
Figure 1:
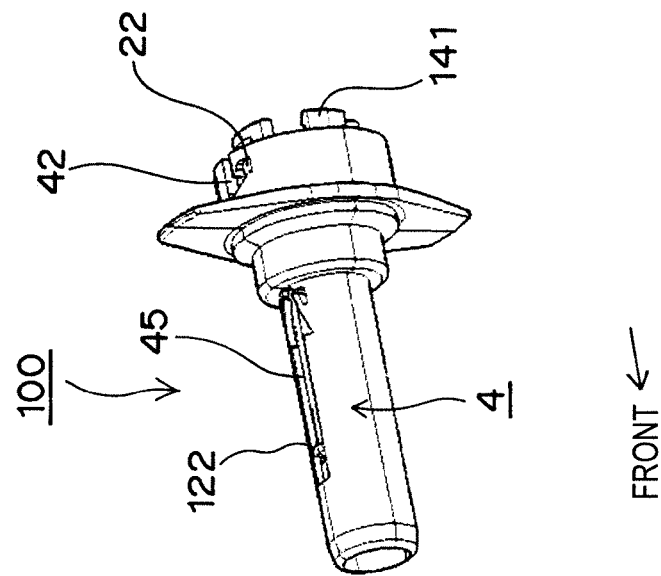
Figure 2:
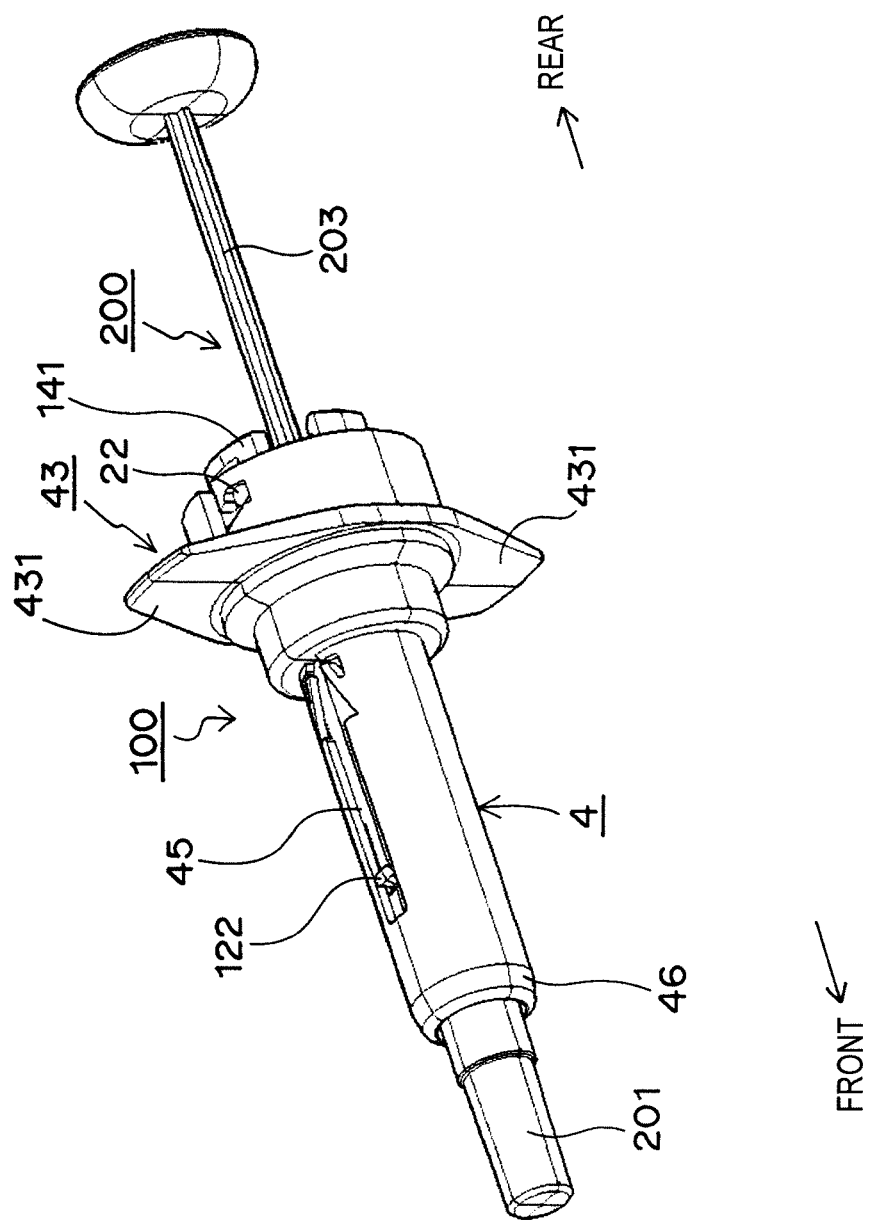
FIG. 2 is a perspective view showing a state in which the protecting device is mounted on a syringe.
Figure 3:
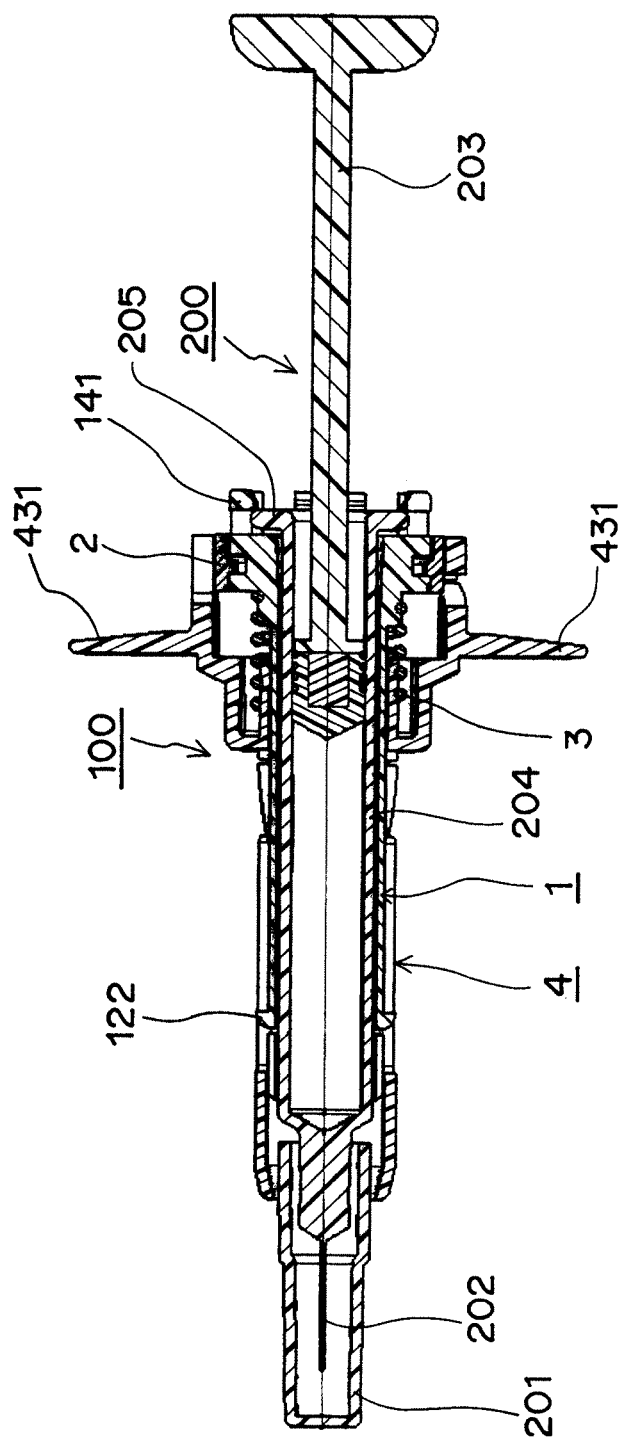
FIG. 3 is a side sectional view showing the state shown in FIG. 2.
Figure 4:
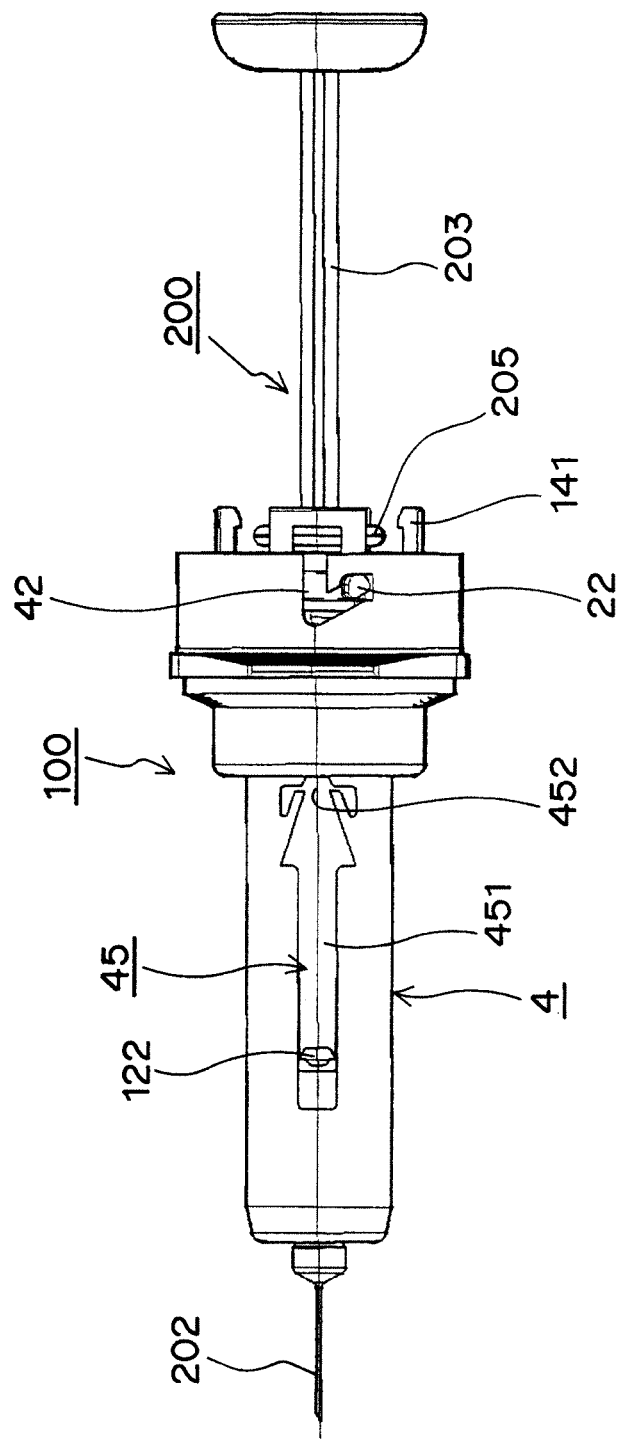
FIG. 4 is a plan view showing the state shown in FIG. 2.
Figure 5:
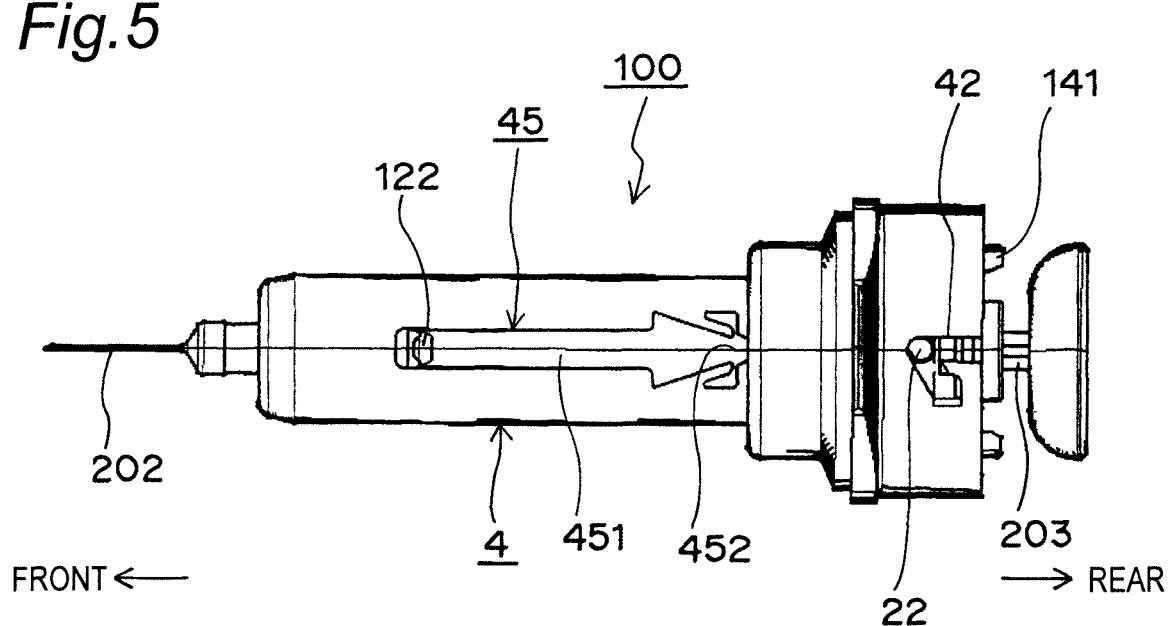
FIG. 5 is a plan view showing a state in which, after the plunger rod of the syringe is pressed and a medicinal solution is administered, the plunger rod is further pressed.
Figure 6:
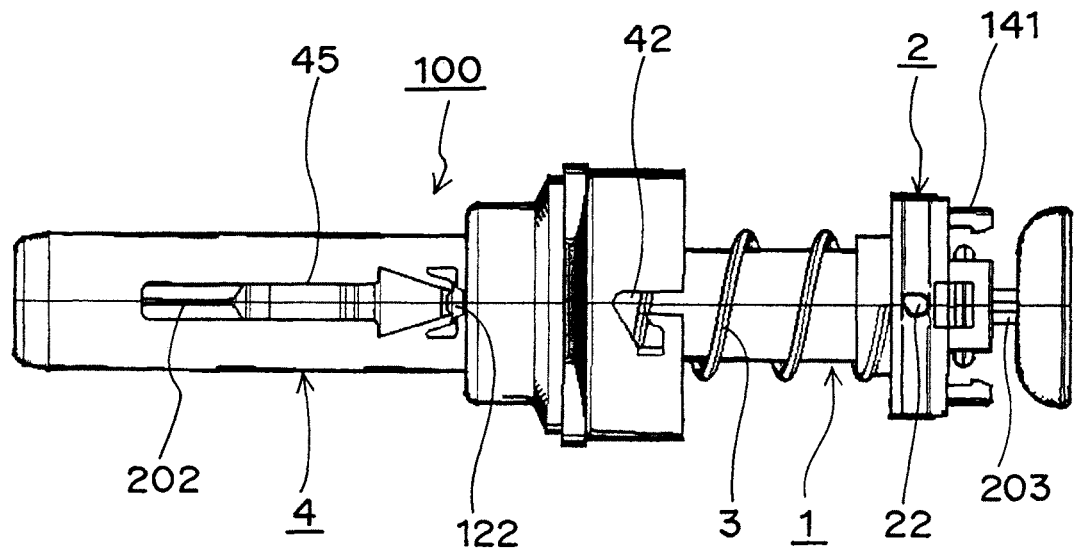
FIG. 6 is a plan view showing a state in which the protecting device has operated and a syringe needle has been stored in the protecting device.

FIG. 1 is a perspective view showing a state in which a syringe protecting device according to this embodiment is just before being mounted on a syringe. In FIG. 1, a syringe protecting device 100 and a syringe 200 are arranged on a straight line. The syringe 200 is a prefilled syringe and the syringe needle 202 (see FIG. 3) at the tip end thereof is covered with a cap 201. FIG. 2 is a perspective view showing a state in which the protecting device 100 is mounted on the syringe 200. FIG. 3 is a side sectional view showing the state shown in FIG. 2. The syringe 200 is inserted into the protecting device 100 and is fixed thereto. FIG. 4 is a plan view showing the state shown in FIG. 2. The cap 201 is removed in the state shown in FIG. 4. FIG. 5 is a plan view showing a state in which, after the plunger rod 203 of the syringe 200 is pressed and the administration of a medicinal solution is completed, the plunger rod 203 is further pressed. FIG. 6 is a plan view showing a state in which the protecting device 100 has operated and the syringe needle 202 has been stored in the protecting device 100. When the protecting device 100 is mounted on the syringe 200 and used in this way, the protecting device 100 operates so as to store the syringe needle 202 after the administration of the medical solution.

Figure 7:
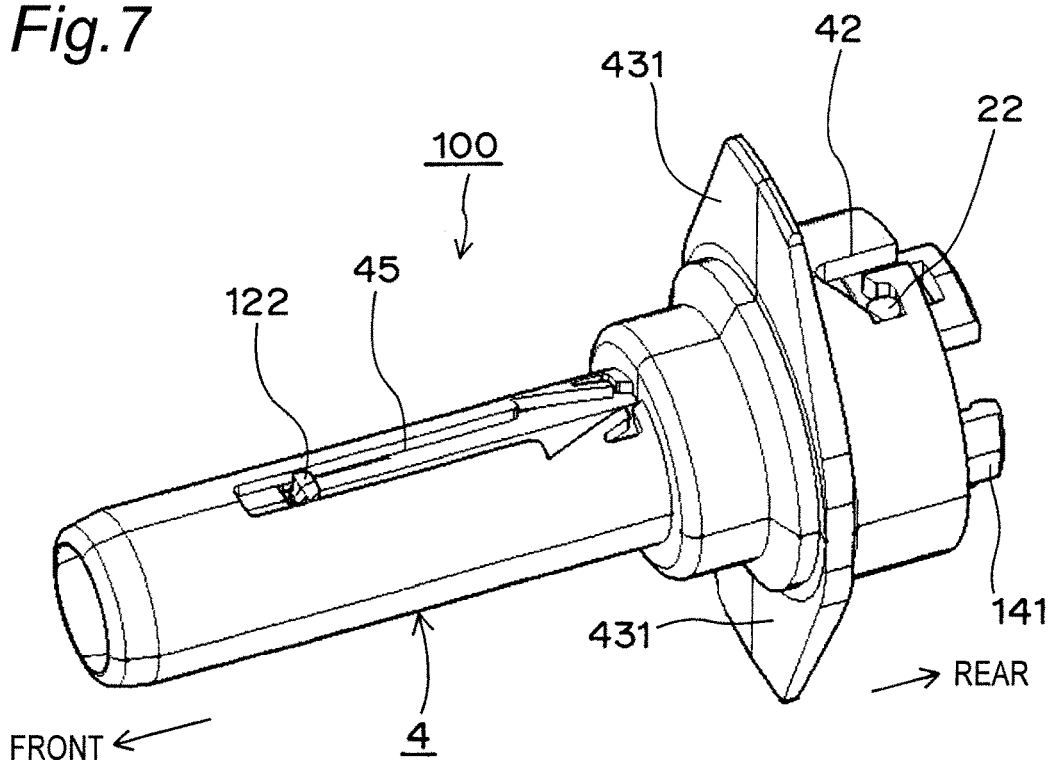
FIG. 7 is an overall front perspective view showing the protecting device.
Figure 8:
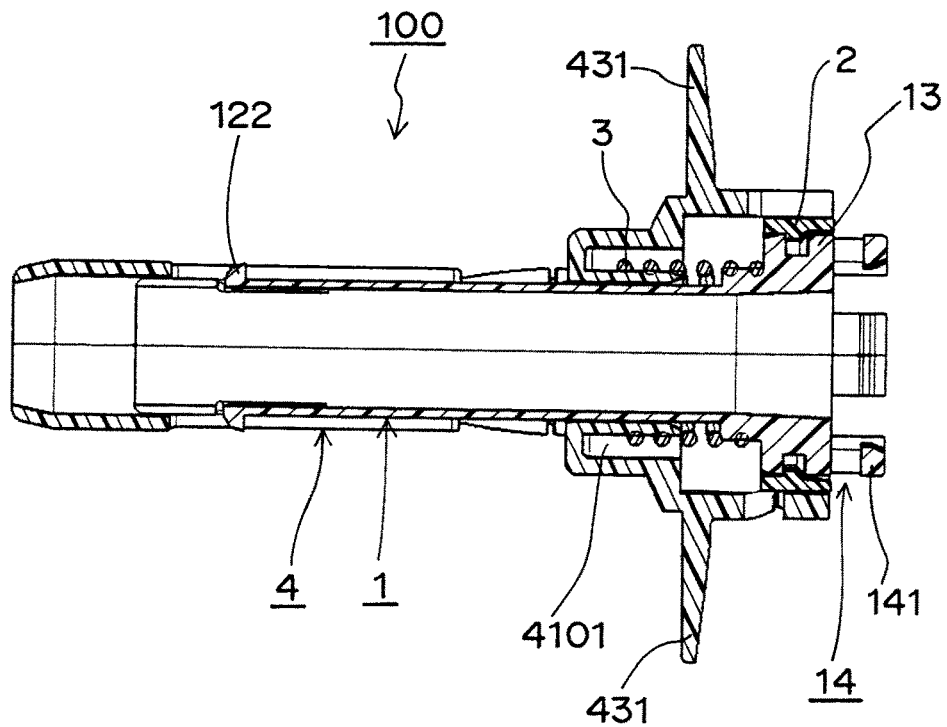
FIG. 8 is a side sectional view showing the protecting device.
Figure 9:
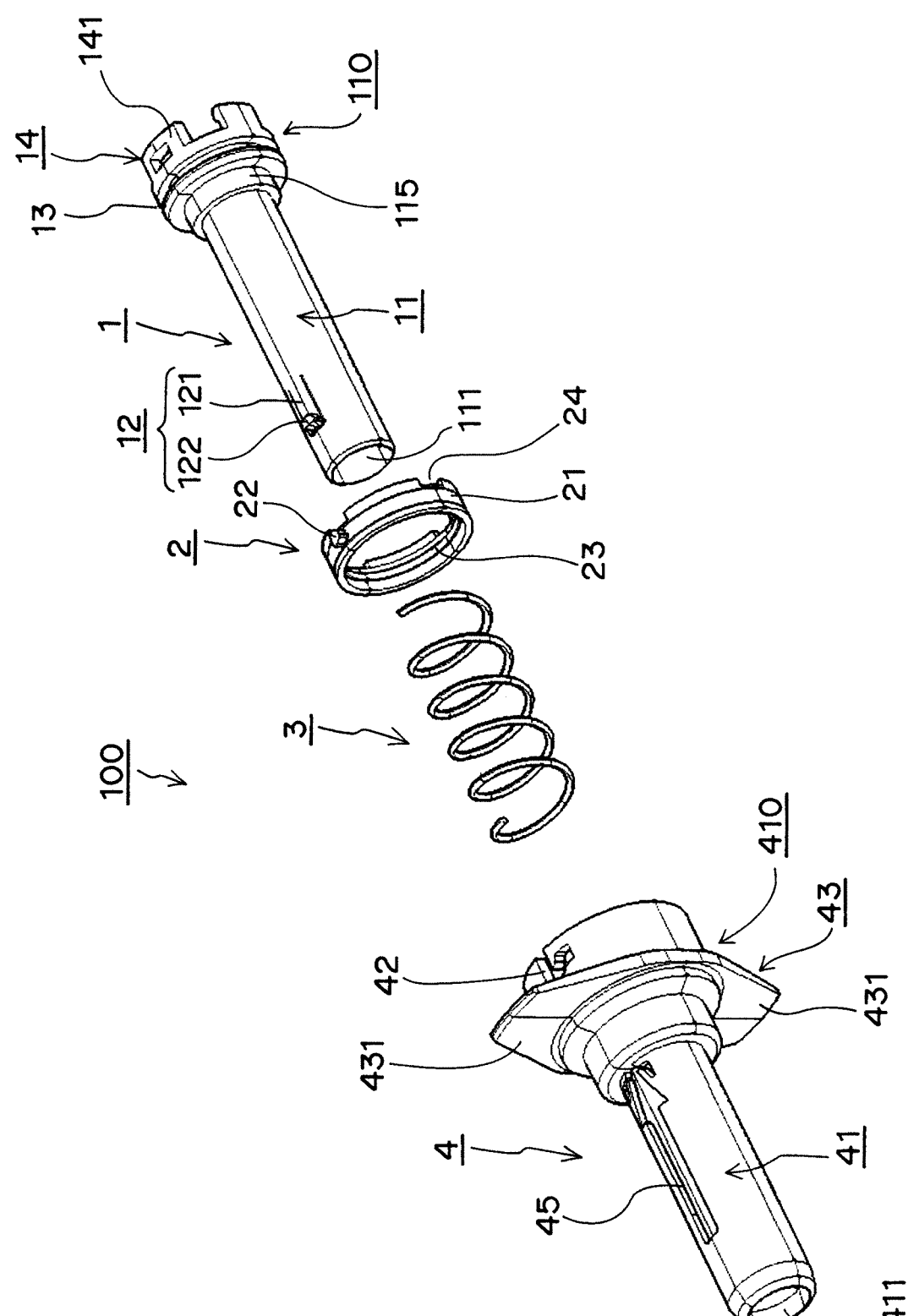
FIG. 9 is an exploded perspective view showing the protecting device.

FIG. 7 is an overall front perspective view showing the protecting device 100. FIG. 8 is a side sectional view showing the protecting device 100. FIG. 9 is an exploded perspective view showing the protecting device 100. The protecting device 100 is composed of an inner cylinder 1, a ring 2, a spring 3 and an outer cylinder 4. The inner cylinder 1 is a member for holding the syringe 200 having been inserted therein. The ring 2 is a member constituting a pre-locking mechanism for fixing the inner cylinder 1 having been inserted into the outer cylinder 4 to the outer cylinder 4. The pre-locking mechanism is a mechanism for preventing the protecting device 100 from operating at an unintended time before use (that is, from malfunctioning). The spring 3 is a member that operates so as to move the inner cylinder 1 rearward with respect to the outer cylinder 4 when the protecting device 100 operates, that is, when the pre-locking mechanism is released. The outer cylinder 4 is a member having an internal space into which the syringe needle 202 of the syringe 200 having been moved rearward together with the inner cylinder 1 is stored. The inner cylinder 1 and the outer cylinder 4 are preferably made of transparent resin. With this configuration, the state of the medical solution in the syringe 200 having been inserted in the protecting device 100 can be visually recognized excellently. For example, polycarbonate resin, cycloolefin resin, and polypropylene resin etc. can be used as the transparent resin.

Figure 10:
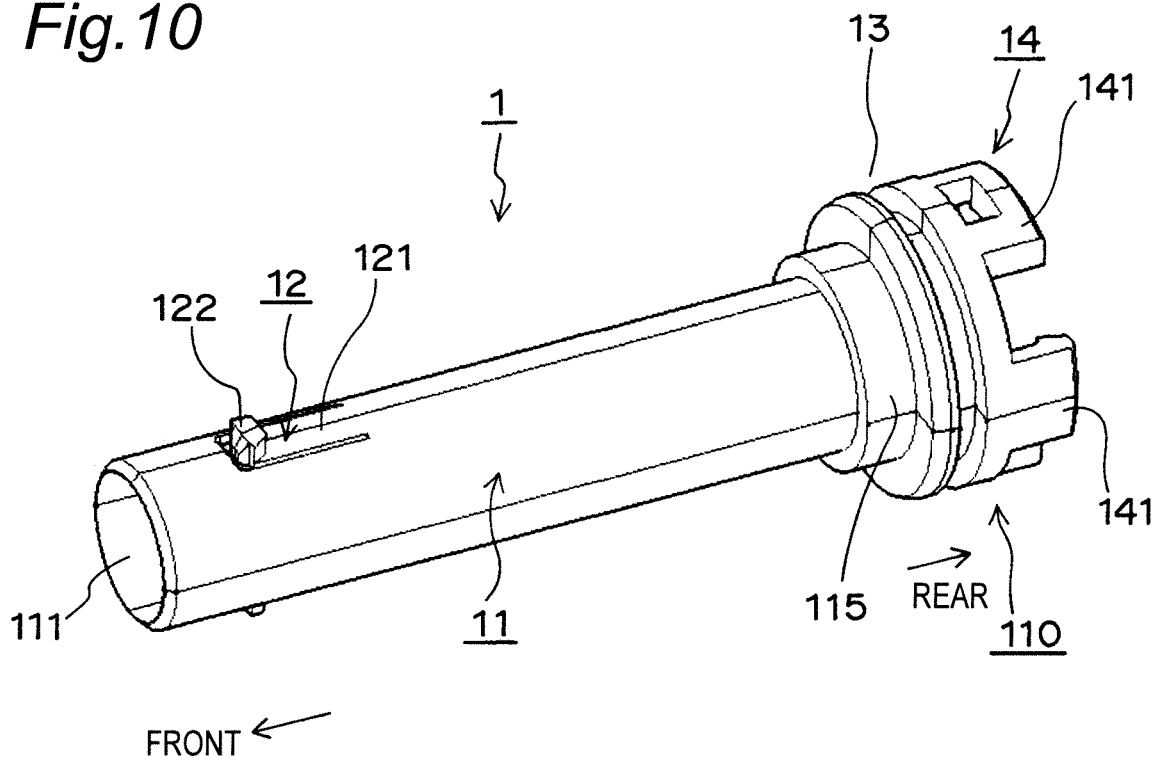
FIG. 10 is a front perspective view showing an inner cylinder.
Figure 11:
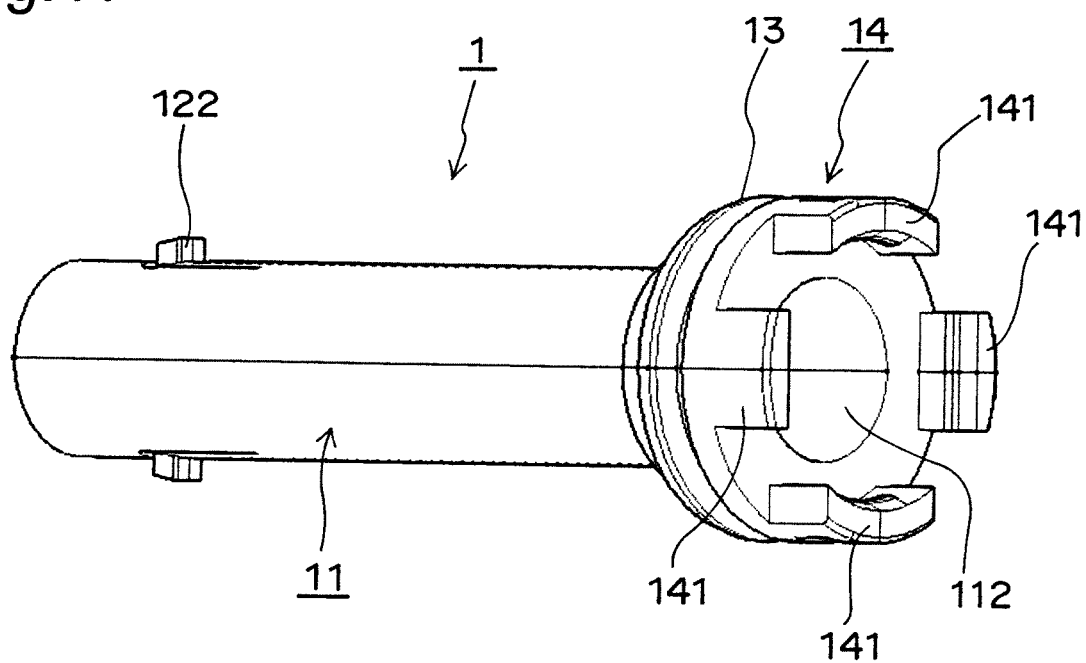
FIG. 11 is a rear perspective view showing the inner cylinder.
Figure 12:
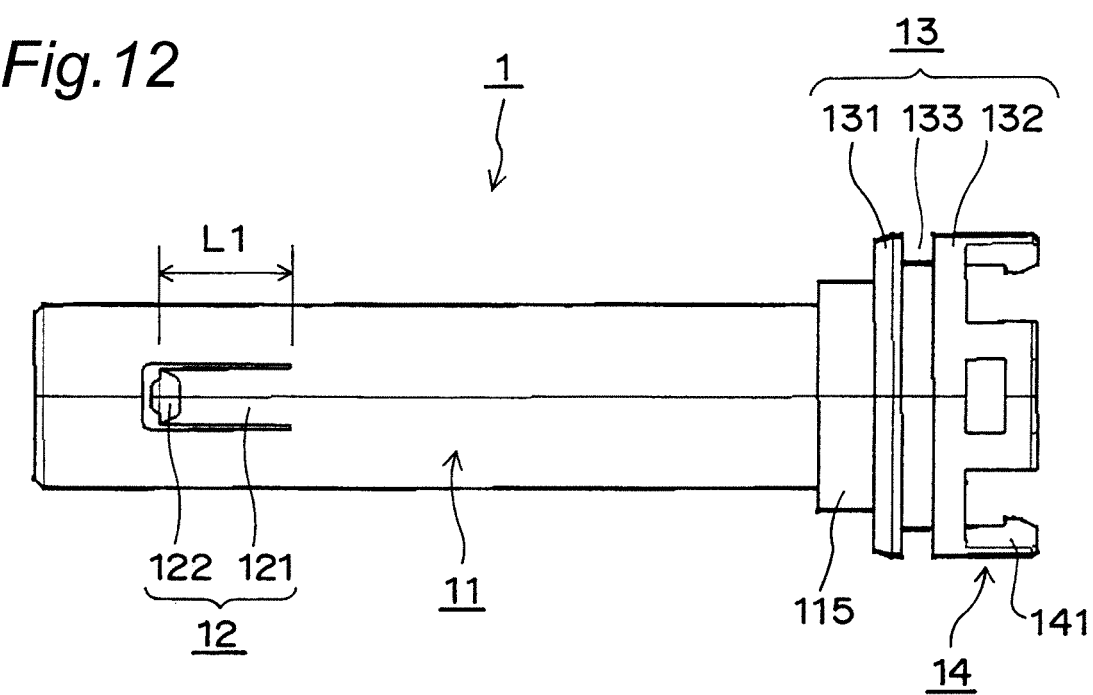
FIG. 12 is a plan view showing the inner cylinder.
Figure 13:
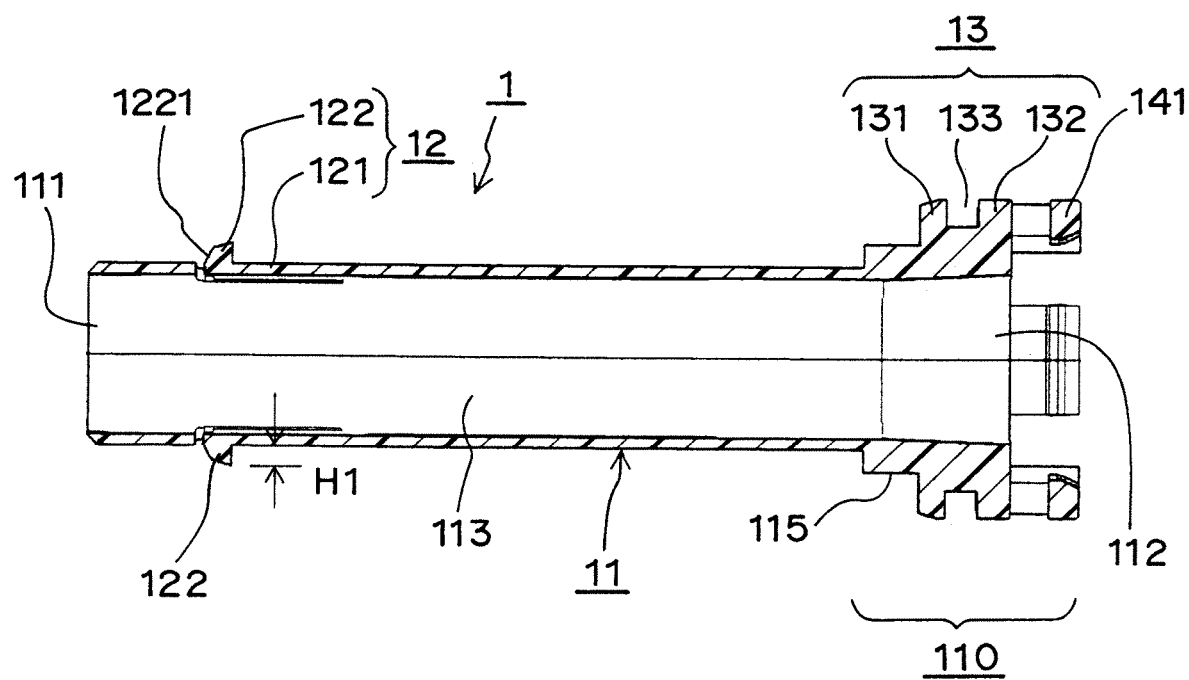
FIG. 13 is a side sectional view showing the inner cylinder.

FIG. 10 is a front perspective view showing the inner cylinder 1. FIG. 11 is a rear perspective view showing the inner cylinder 1. FIG. 12 is a plan view showing the inner cylinder 1. FIG. 13 is a side sectional view showing the inner cylinder 1. The inner cylinder 1 has a cylindrical body 11, tongue sections 12, a ring mounting section 13, and a flange mounting section 14. A large diameter section 110 is formed at the rear section of the inner cylinder 1, and the ring mounting section 13 and the flange mounting section 14 are provided on the large diameter section 110.

The cylindrical body 11 has a front end opening 111 and a rear end opening 112 and also has an inner space 113 into which the syringe 200 is inserted. The tongue sections 12 are formed in the front section of the cylindrical body 11 and serve as elements constituting a post-locking mechanism for fixing the inner cylinder 1 having been moved rearward to the outer cylinder 4. The post-locking mechanism is a mechanism for preventing the syringe needle 202 having been stored in the protecting device 100 after operation from being exposed. The tongue sections 12, two in number, are formed at positions opposed to each other in the circumferential direction of the cylindrical body 11. The tongue section 12 is composed of a tongue piece 121 that can be elastically deformable inward and outward while the rear end thereof is used as the base end and an outward protruding section 122 formed at the front end section of the tongue piece 121. The tongue piece 121 is formed by cutting out part of the peripheral wall of the cylindrical body 11. The protruding section 122 has a trapezoidal shape in a plan view. The ring mounting section 13 is composed of a front wall section 131, a rear wall section 132, and a circumferential groove section 133 provided therebetween. The flange mounting section 14 has pawl sections 141 protruding rearward to fix the flange 205 of the syringe body 204 of the syringe 200 to the inner cylinder 1.

Figure 14:
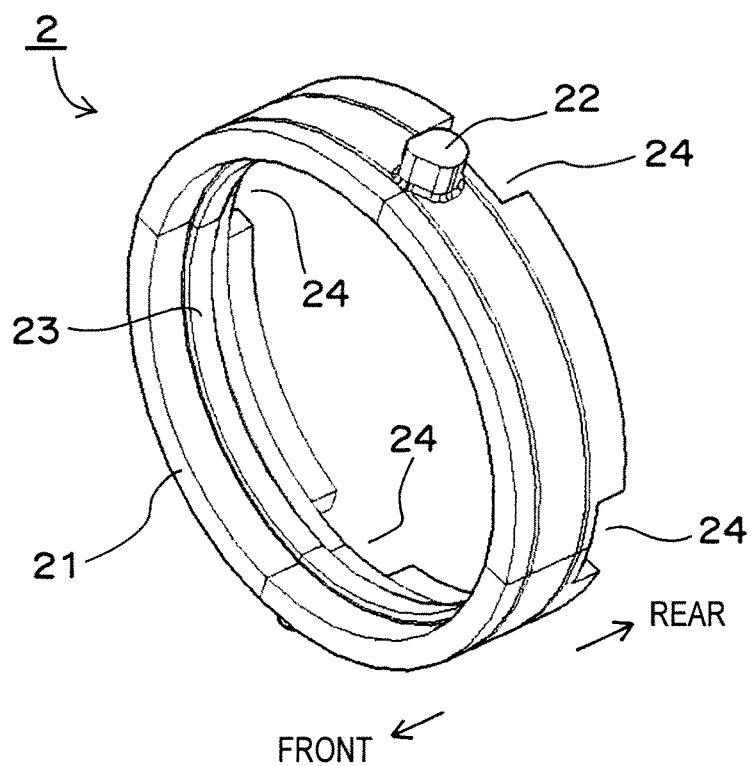
FIG. 14 is a front perspective view showing a ring.
Figure 15:
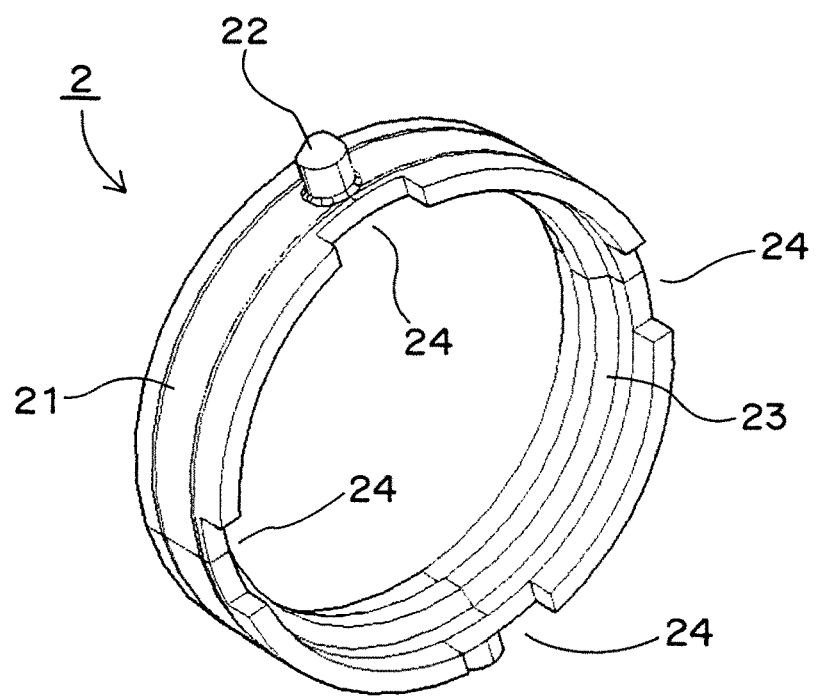
FIG. 15 is a rear perspective view showing the ring.
Figure 16:
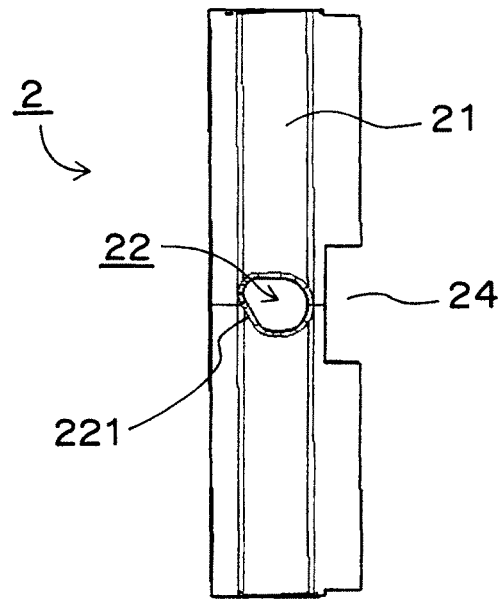
FIG. 16 is a plan view showing the ring.
Figure 17:
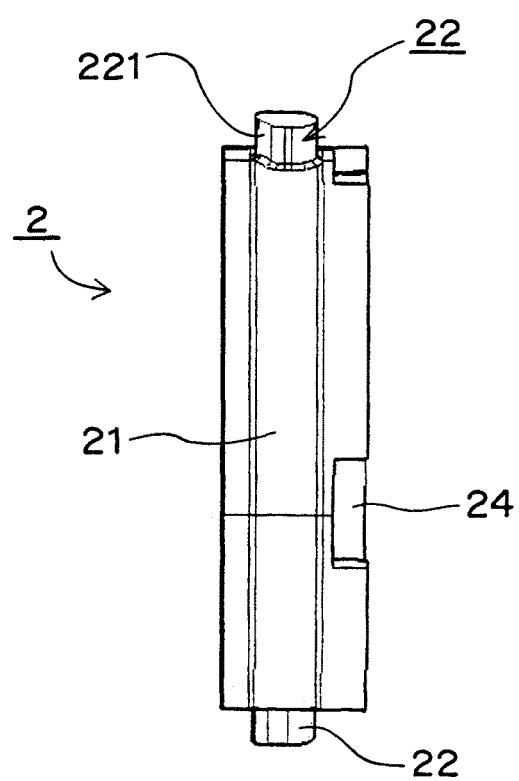
FIG. 17 is a side view showing the ring.
Figure 18:
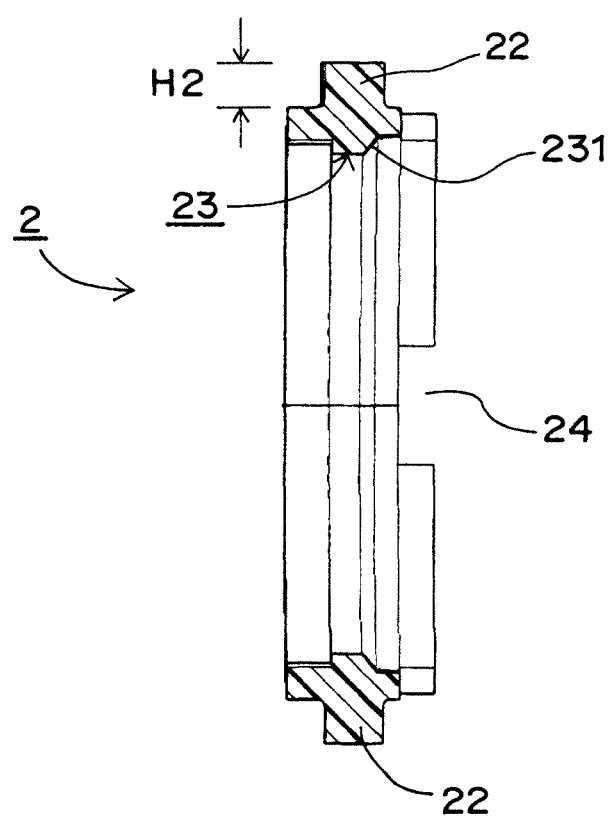
FIG. 18 is a side sectional view showing the ring.

FIG. 14 is a front perspective view showing the ring 2. FIG. 15 is a rear perspective view showing the ring 2. FIG. 16 is a plan view showing the ring 2. FIG. 17 is a side view showing the ring 2. FIG. 18 is a side sectional view showing the ring 2. The ring 2 has a cylindrical body 21, protruding sections 22 provided outward on the outer circumferential face of the cylindrical body 21, a circumferentially protruding section 23 provided inward on the inner circumferential face of the cylindrical body 21, and cut-out sections 24 provided at the rear edge of the cylindrical body 21. The protruding sections 22, two in number, are provided at positions opposed to each other in the circumferential direction of the cylindrical body 21. The protruding section 22 has a nearly circular shape in a plan view. The cut-out sections 24 are formed at four positions in the circumferential direction at equal intervals.

Figure 19:
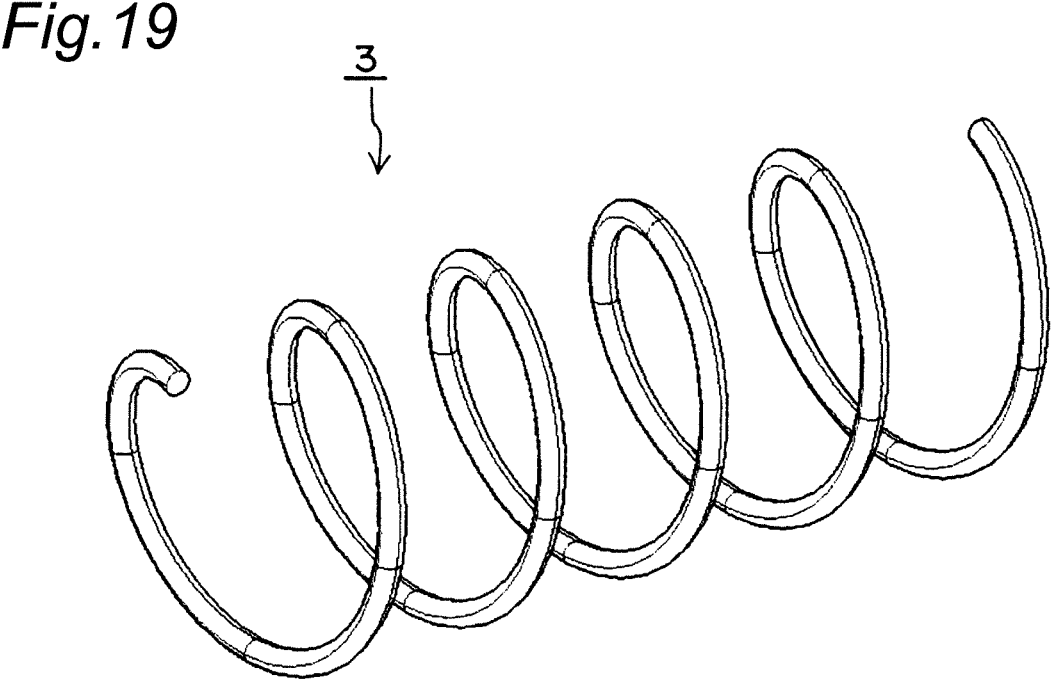
FIG. 19 is a perspective view showing a spring in a no-load state.
Figure 20:
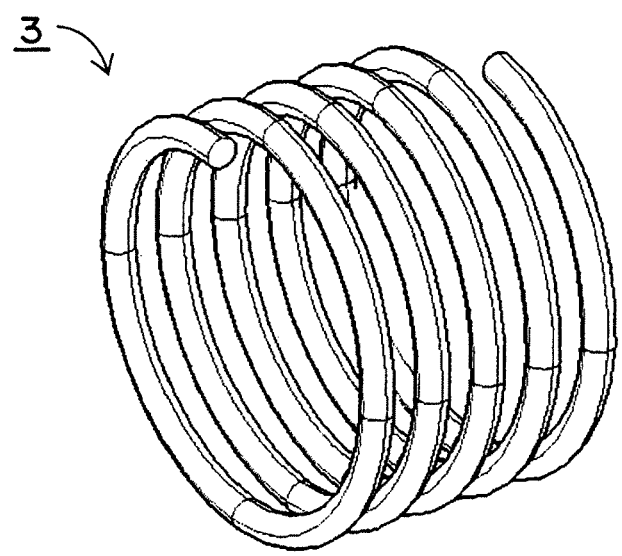
FIG. 20 is a perspective view showing the spring in a compressed state.

FIG. 19 is a perspective view showing the spring 3 in a no-load state. FIG. 20 is a perspective view showing the spring 3 in a compressed state. The spring 3 has an inside diameter to be fitted on the circumferential face 115 of the large diameter section 110 of the inner cylinder 1.

Figure 21:
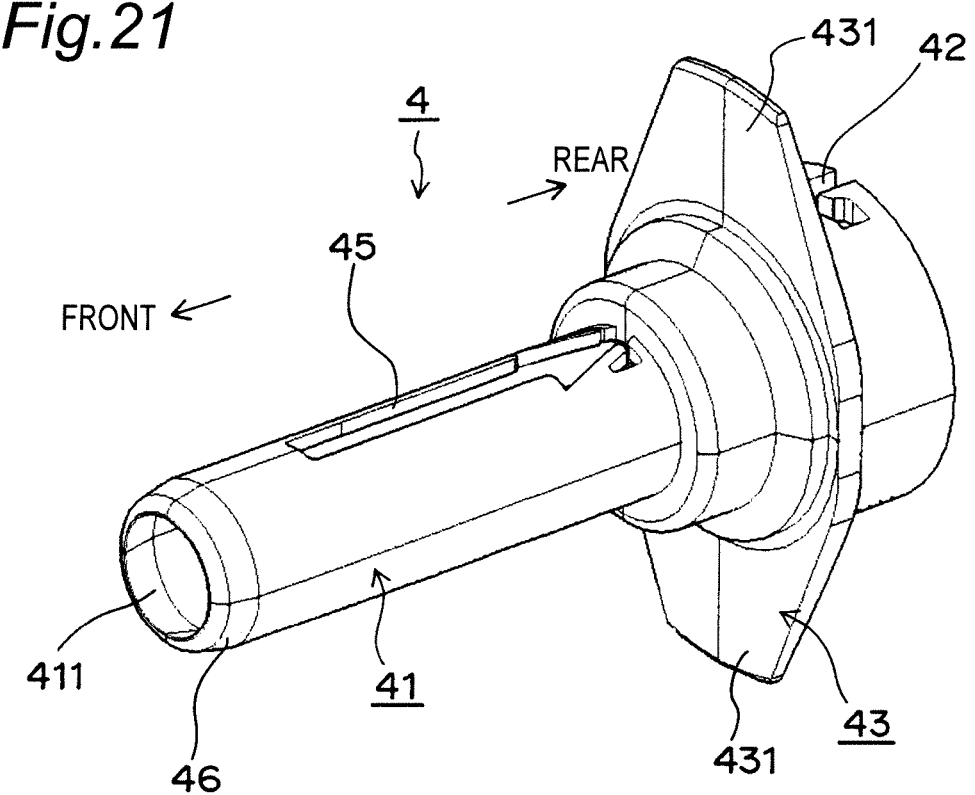
FIG. 21 is a front perspective view showing an outer cylinder.
Figure 22:
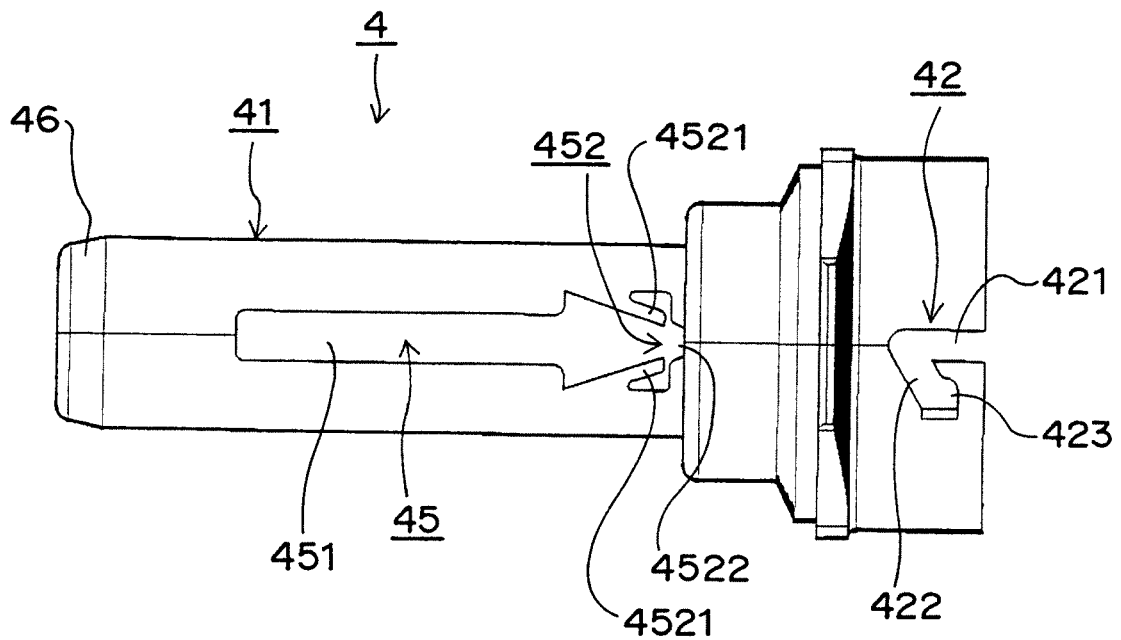
FIG. 22 is a plan view showing the outer cylinder.
Figure 23:
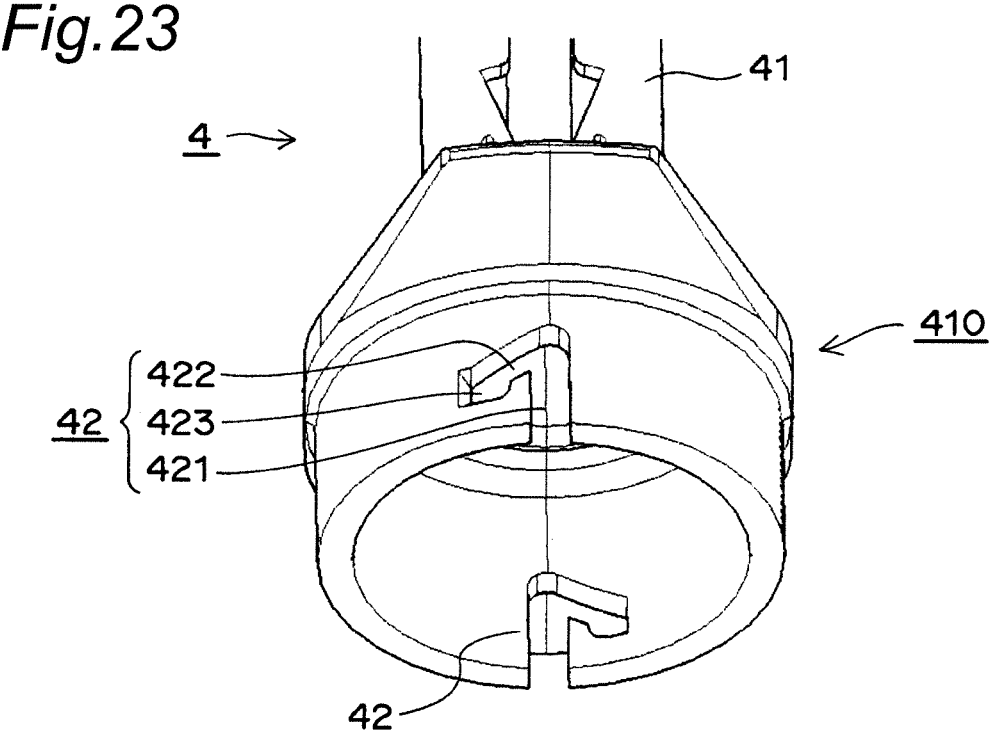
FIG. 23 is a rear perspective view showing the outer cylinder.
Figure 24:
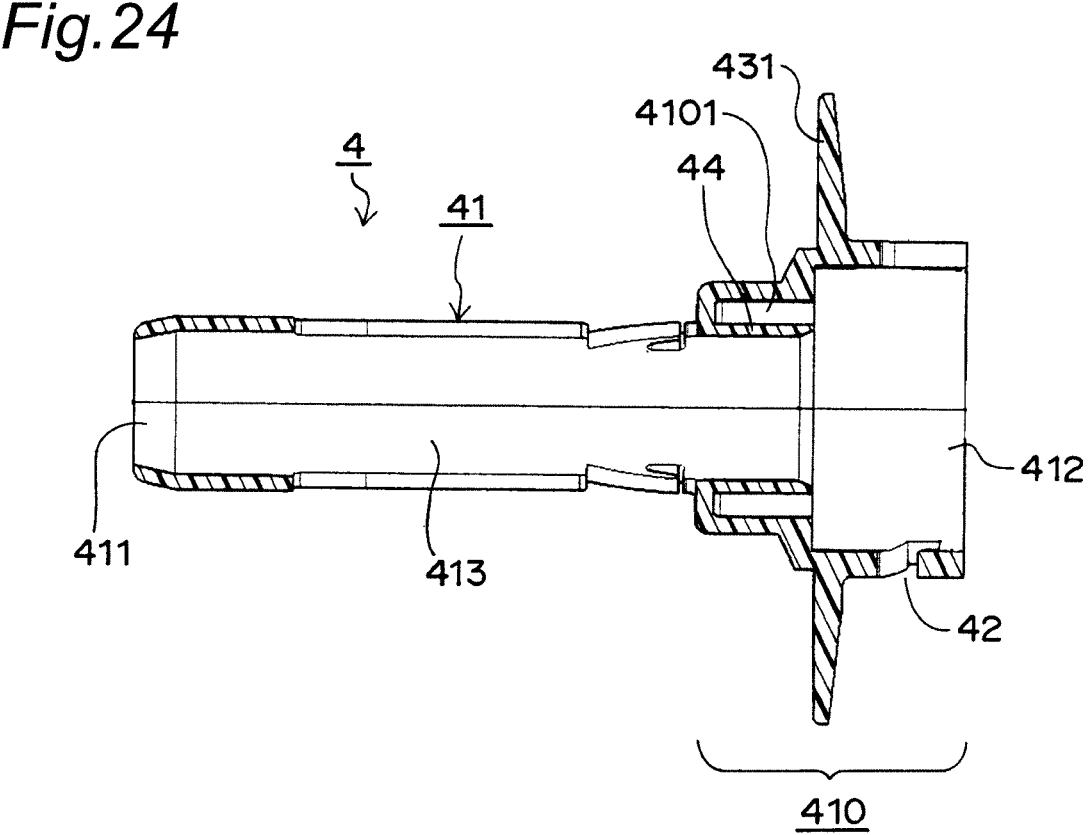
FIG. 24 is a side sectional view showing the outer cylinder.

FIG. 21 is a front perspective view showing the outer cylinder 4. FIG. 22 is a plan view showing the outer cylinder 4. FIG. 23 is a rear perspective view showing the outer cylinder 4. FIG. 24 is a side sectional view showing the outer cylinder 4. The outer cylinder 4 has a cylindrical body 41, through groove sections 42, a flange section 43, a spring supporting section 44, and slide groove sections 45. A large diameter section 410 is formed at the rear section of the outer cylinder 4, and the through groove sections 42, the flange section 43, and the spring supporting section 44 are provided in the large diameter section 410.

The cylindrical body 41 has a front end opening 411 and a rear end opening 412 and also has an internal space 413 into which the inner cylinder 1 is inserted. The large diameter section 110 of the inner cylinder 1 is inserted into the large diameter section 410 of the outer cylinder 4. The through groove sections 42 and the ring 2 are elements constituting the pre-locking mechanism. The through groove section 42 is composed of a straight section 421 being open to the rear end edge thereof and extended in the front-rear direction, an inclined section 422 extended obliquely rearward from the front end of the straight section 421, and an engaging section 423 extended linearly rearward from the rear end of the inclined section 422. The through groove sections 42 are formed at two positions opposed to each other in the circumferential direction of the rear section of the outer cylinder 4. The flange section 43 has two side sections 431 extended perpendicularly with respect to the cylindrical body 41 in directions opposed to each other. The spring supporting section 44 is composed of a circumferential wall that is formed inside the large diameter section 410 so as to support the spring 3 from the inside. A space 4101 for accommodating the front section of the spring 3 is formed inside the large diameter section 410 by the spring supporting section 44.

The slide groove sections 45 and the tongue sections 12 of the inner cylinder 1 are elements constituting the post-locking mechanism. The slide groove sections 45, two in number, are formed so as to be extended in the front-rear direction from the central section to the front section of the cylindrical body 41 at positions opposed to each other in the circumferential direction of the cylindrical body 41. The slide groove section 45 is composed of a groove body 451 and an engaging section 452 formed at the rear end section of the groove body 451. The slide groove section 45 is formed so that, in the state in which the inner cylinder 1 is fixed to the outer cylinder 4 before the inner cylinder 1 is moved rearward, that is, before the protecting device 100 is operated, the protruding section 122 of the tongue section 12 is positioned inside the groove body 451 (see FIG. 7) and so that, in the state in which the inner cylinder 1 has been moved rearward, that is, after the protecting device 100 is operated, the protruding section 122 of the tongue section 12 is engaged with the engaging section 452 so as to be unmovable. The engaging section 452 has two reverse movement preventing pieces 4521 obliquely extended rearward from both the sides thereof and an engaging space 4522. The reverse movement preventing pieces 4521 have elasticity and are formed so as to allow the protruding section 122 of the tongue section 12 to pass from the front side to the rear side, but so as not to allow the protruding section 122 to pass in the opposite direction. Hence, the engaging section 452 is configured so as to unmovably hold the protruding section 122 having passed through the reverse movement preventing pieces 4521 inside the engaging space 4522.

[Assembling Work]

Next, the assembling work of the protecting device 100 will be described.

Figure 25:
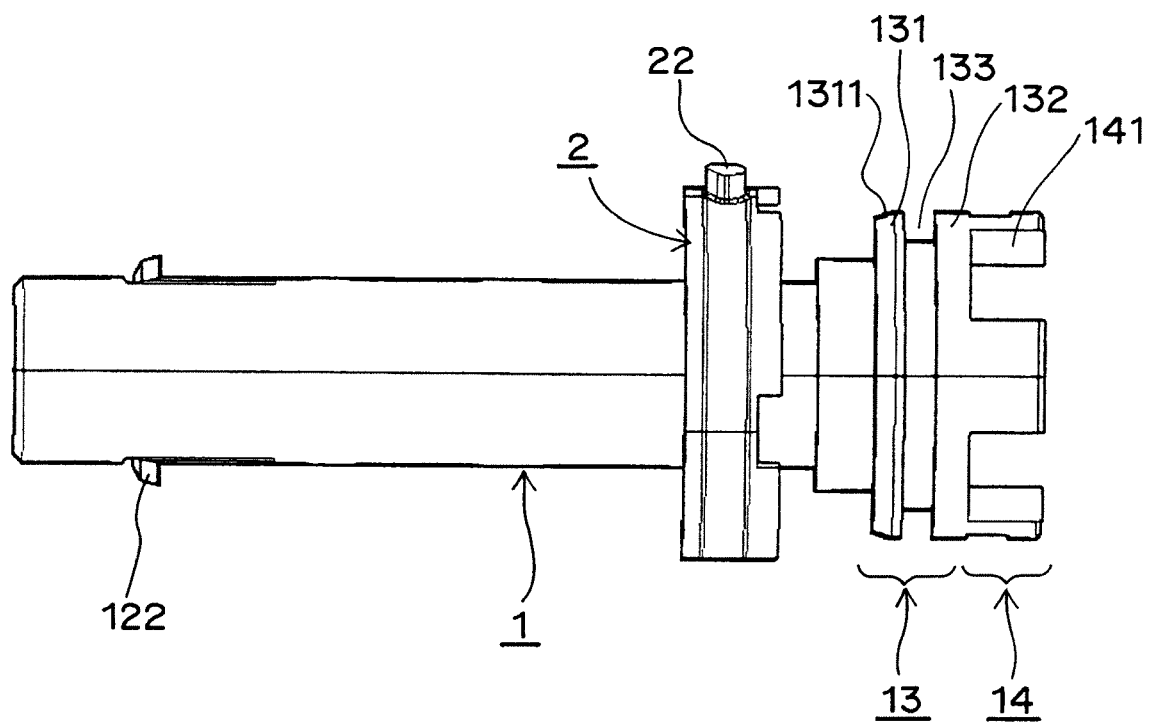
FIG. 25 is a side view showing a state in which the inner cylinder is inserted into the ring.
Figure 26:
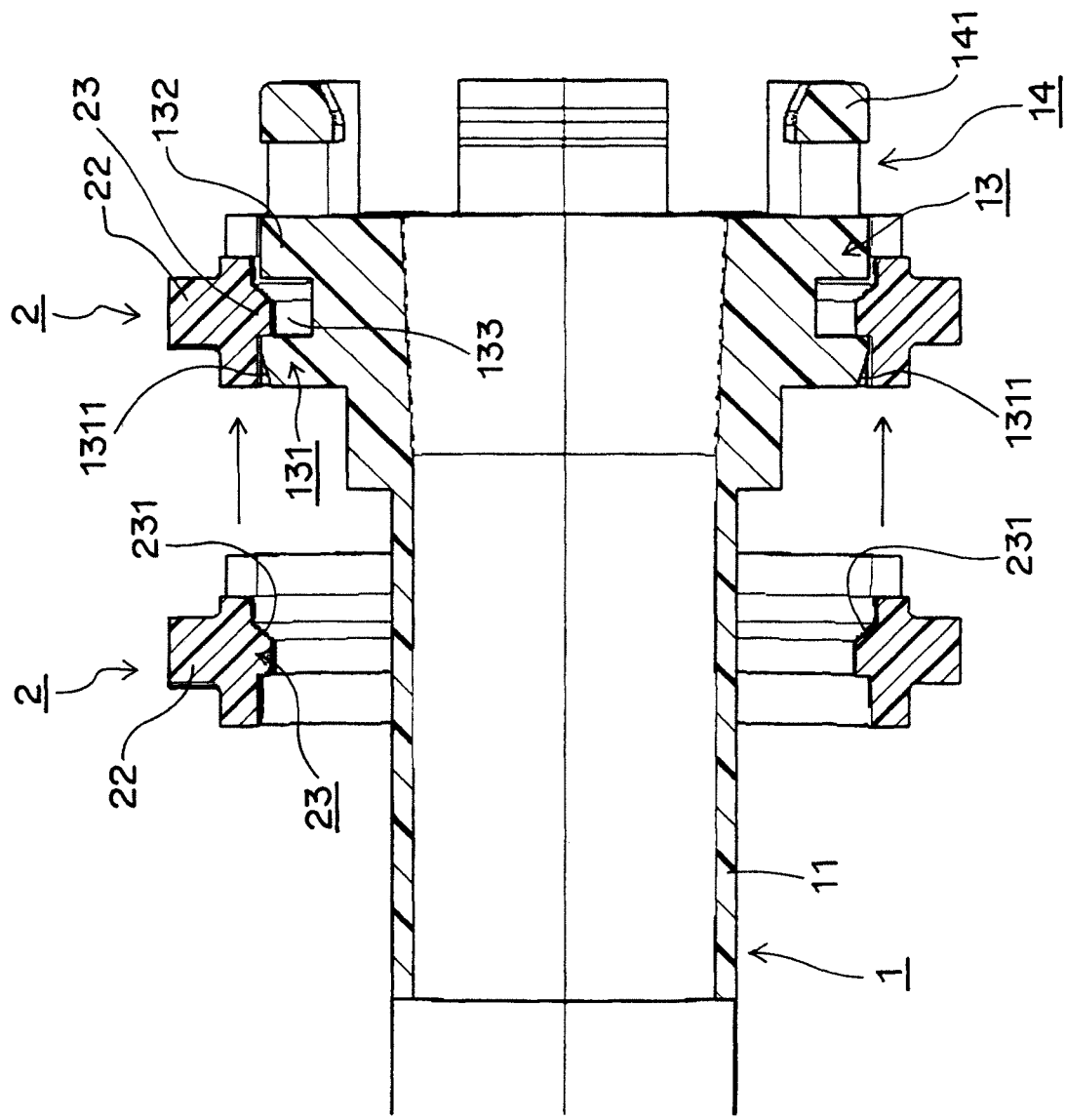
FIG. 26 is a side sectional view showing a state in which the ring is press-fitted on a ring mounting section.
Figure 27:
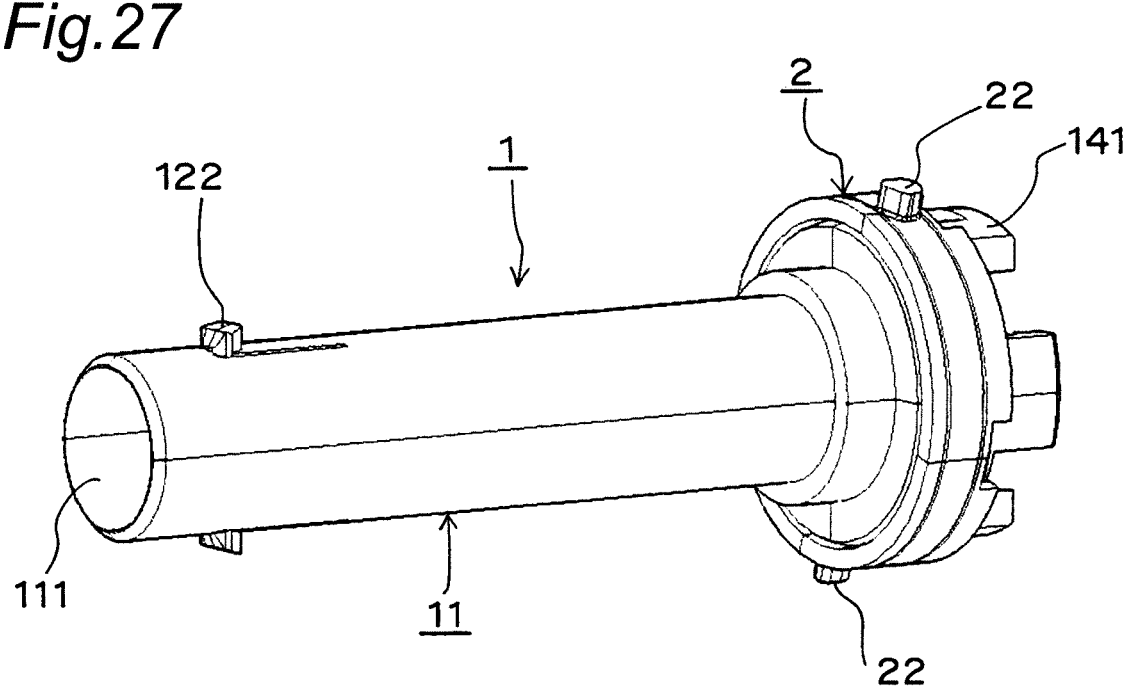
FIG. 27 is a perspective view showing a state in which the ring is mounted on the ring mounting section.

First, as shown in FIG. 25, the inner cylinder 1 is inserted into the ring 2. Next, as shown in FIG. 26, the ring 2 is press-fitted on the ring mounting section 13. FIG. 27 is a perspective view showing a state in which the ring 2 has been mounted on the ring mounting section 13.

Since the front wall section 131 of the ring mounting section 13 has a tapered face 1311 (see FIG. 26) at the front section thereof and since the circumferentially protruding section 23 of the ring 2 has a tapered face 231 (see FIG. 26) at the rear section thereof, the circumferentially protruding section 23 can smoothly climb over the front wall section 131. Hence, the press-fitting work can be performed smoothly. Furthermore, since a clearance in the front-rear direction and a clearance in the inside-outside direction are present between the circumferentially protruding section 23 and the circumferential groove section 133 after the press-fitting work and since the circumferentially protruding section 23 is held between the front wall section 131 and the rear wall section 132, the ring 2 is fitted on the ring mounting section 13 so as to be slidable in the circumferential direction, but so as not to be movable in the front-rear direction, and does not come off from the ring mounting section 13. As a result, the ring 2 is stably mounted on the ring mounting section 13.

Figure 28:
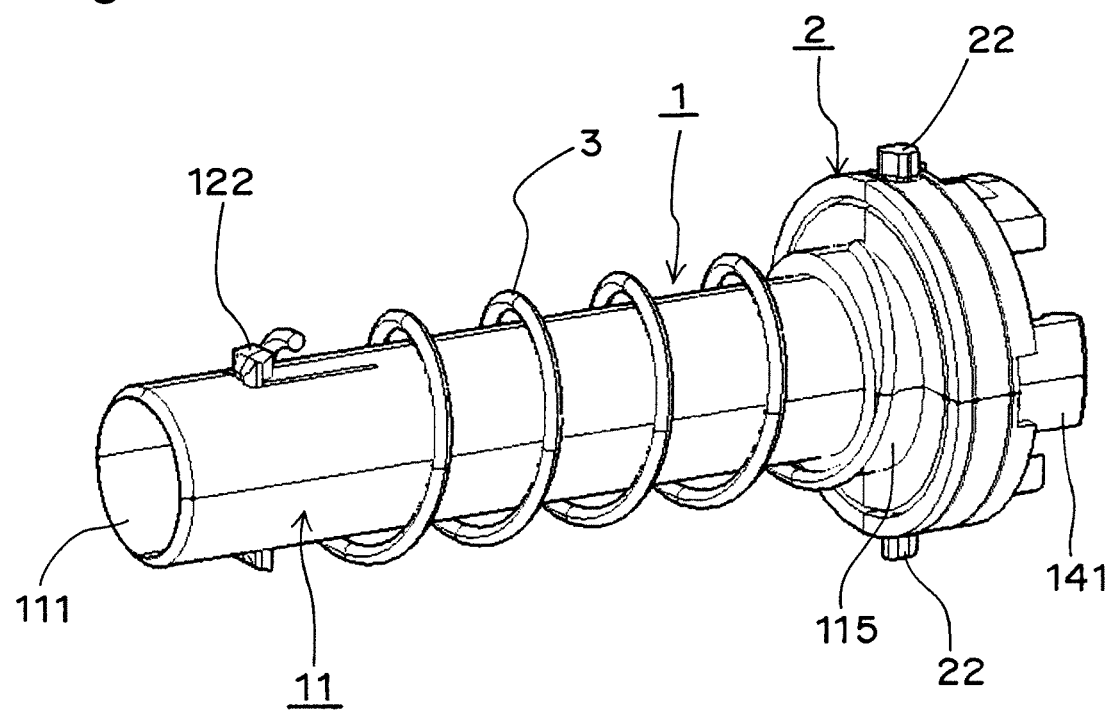
FIG. 28 is a perspective view showing a state in which the inner cylinder on which the ring is mounted is inserted into the spring being in a no-load state.

Next, as shown in FIG. 28, the inner cylinder 1 on which the ring 2 is mounted is inserted into the spring 3 being in a no-load state. At this time, the rear end section of the spring 3 is positioned on the circumferential face 115 of the large diameter section 110.

Figure 29:
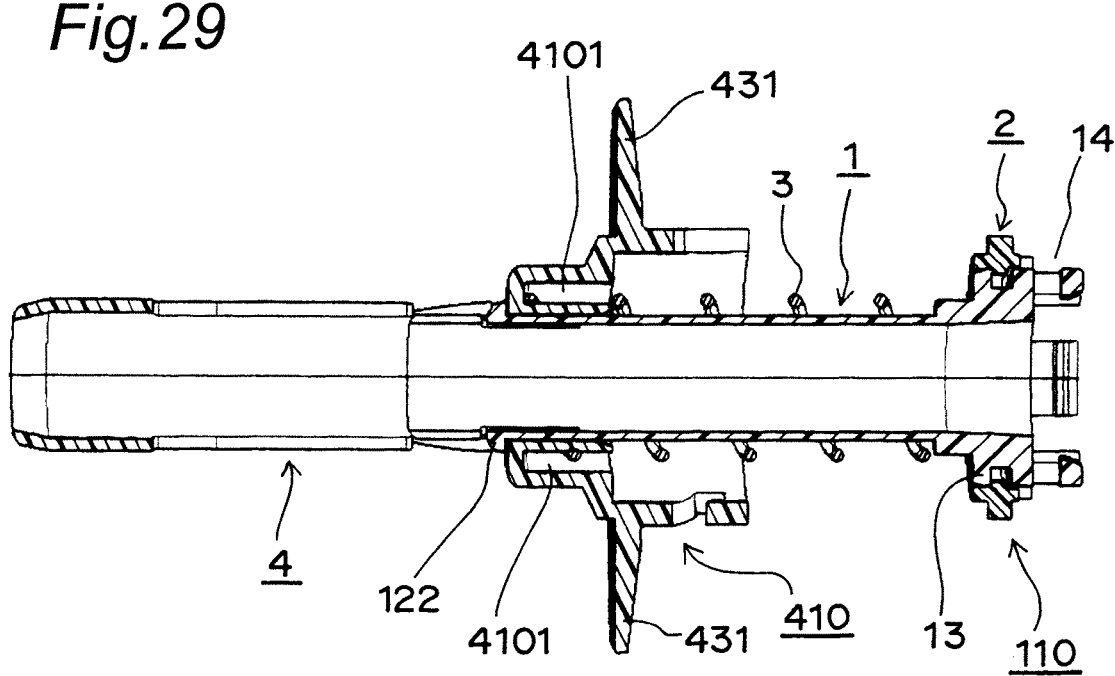
FIG. 29 is a side sectional view showing a state in which the inner cylinder being in the state shown in FIG. 28 is inserted into the outer cylinder.
Figure 30:
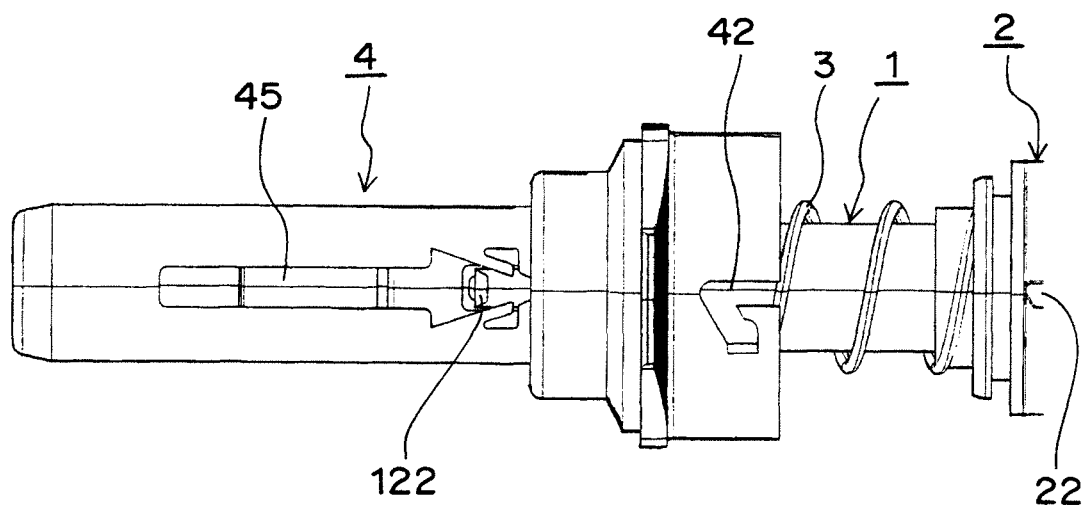
FIG. 30 is a plan view showing the state shown in FIG. 29.

Next, as shown in FIG. 29, the inner cylinder 1 being in the state shown in FIG. 28 is inserted into the outer cylinder 4. FIG. 30 is a plan view showing the state shown in FIG. 29. At this time, the front section of the spring 3 is positioned inside the space 4101. Hence, the spring 3 becomes stable. Since a tapered face 1221 directed outward and rearward (see FIG. 13) is formed on the front section of the protruding section 122, when the inner cylinder 1 is inserted into the outer cylinder 4, the protruding sections 122 smoothly slide along the inner face of the outer cylinder 4 and reach the slide groove sections 45. Consequently, the insertion work of the inner cylinder 1 can be performed smoothly.

Figure 31:
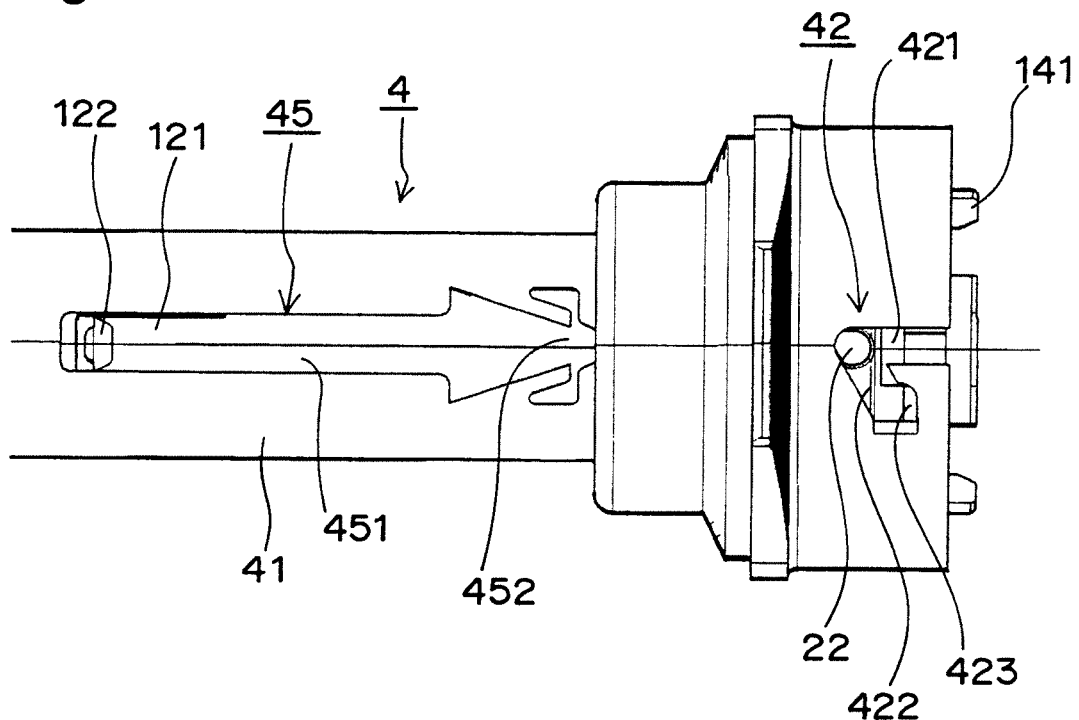
FIG. 31 is a plan view showing a state in which the inner cylinder being in the state shown in FIG. 30 is further pushed into the outer cylinder.

Next, as shown in FIG. 31, the inner cylinder 1 being in the state shown in FIG. 30 is further pushed into the outer cylinder 4, whereby the protruding sections 22 of the ring 2 are inserted into the straight sections 421 of the through groove sections 42. Hence, the spring 3 is going to be compressed in a state of being positioned in the space 4101 inside the large diameter section 410. At this time, since the front section of the spring 3 is positioned inside the space 4101, the spring 3 is going to be compressed stably.

Figure 32:
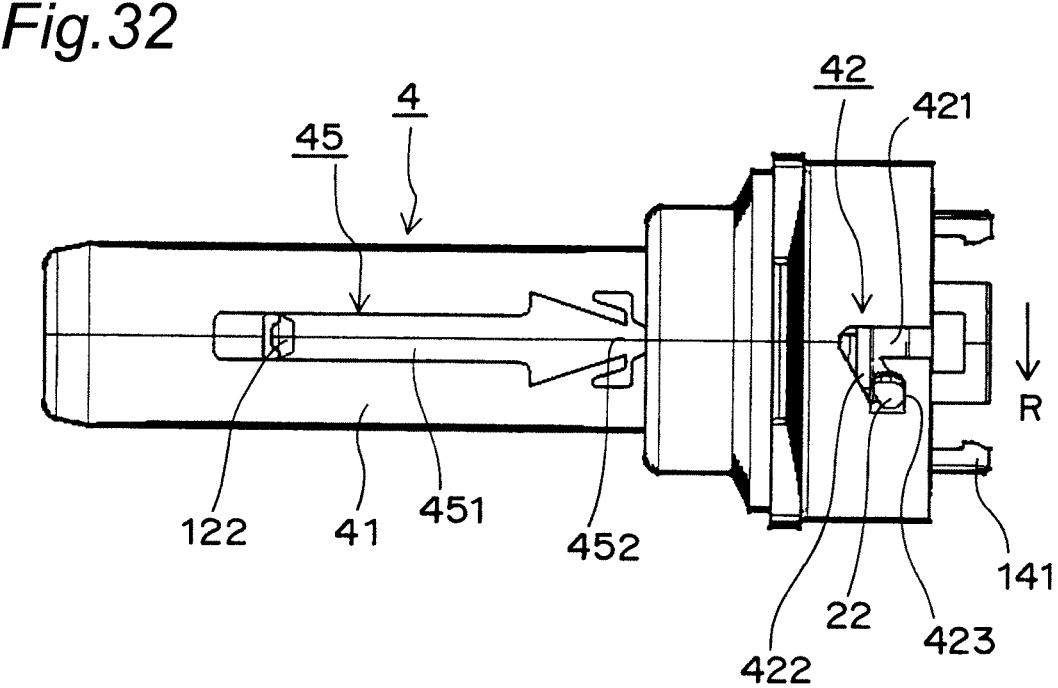
FIG. 32 is a plan view showing a state in which a protruding section is positioned at the engaging section of a through groove section.

Next, as shown in FIG. 32, the ring 2 is slightly rotated in the direction of arrow R, whereby the protruding section 22 passes through the inclined section 422 and is positioned at the engaging section 423. At this time, since the rotating work of the ring 2 can be performed by hooking fingers or a jig on the cut-out sections 24 (see FIG. 15) at the rear edge of the cylindrical body 21, the rotating work can be performed easily. Furthermore, since the inner cylinder 1, that is, the ring 2, is energized rearward by the compressed spring 3, the protruding section 22 passes through the inclined section 422 and moves to the engaging section 423 easily by merely slightly rotating the ring 2 in the direction of arrow R.

Moreover, since the engaging section 423 is extended linearly rearward from the rear end of the inclined section 422, the protruding section 22 is positioned inside the engaging section 423 in a state of being unmovable in the circumferential direction and in a state of being energized rearward. Hence, the protruding section 22 is configured so as not to easily come off from the engaging sections 423, whereby malfunction hardly occurs. In other words, with the pre-locking mechanism composed of the ring 2 and the through groove sections 42, since the protruding sections 22 can be firmly held by the engaging sections 423, the inner cylinder 1 before use can be firmly fixed to the outer cylinder 4, whereby malfunction can be prevented.

The protecting device 100 is assembled as described above.

[Mounting Work]

Next, the mounting work of the protecting device 100 on the syringe 200 will be described.

Figure 33:
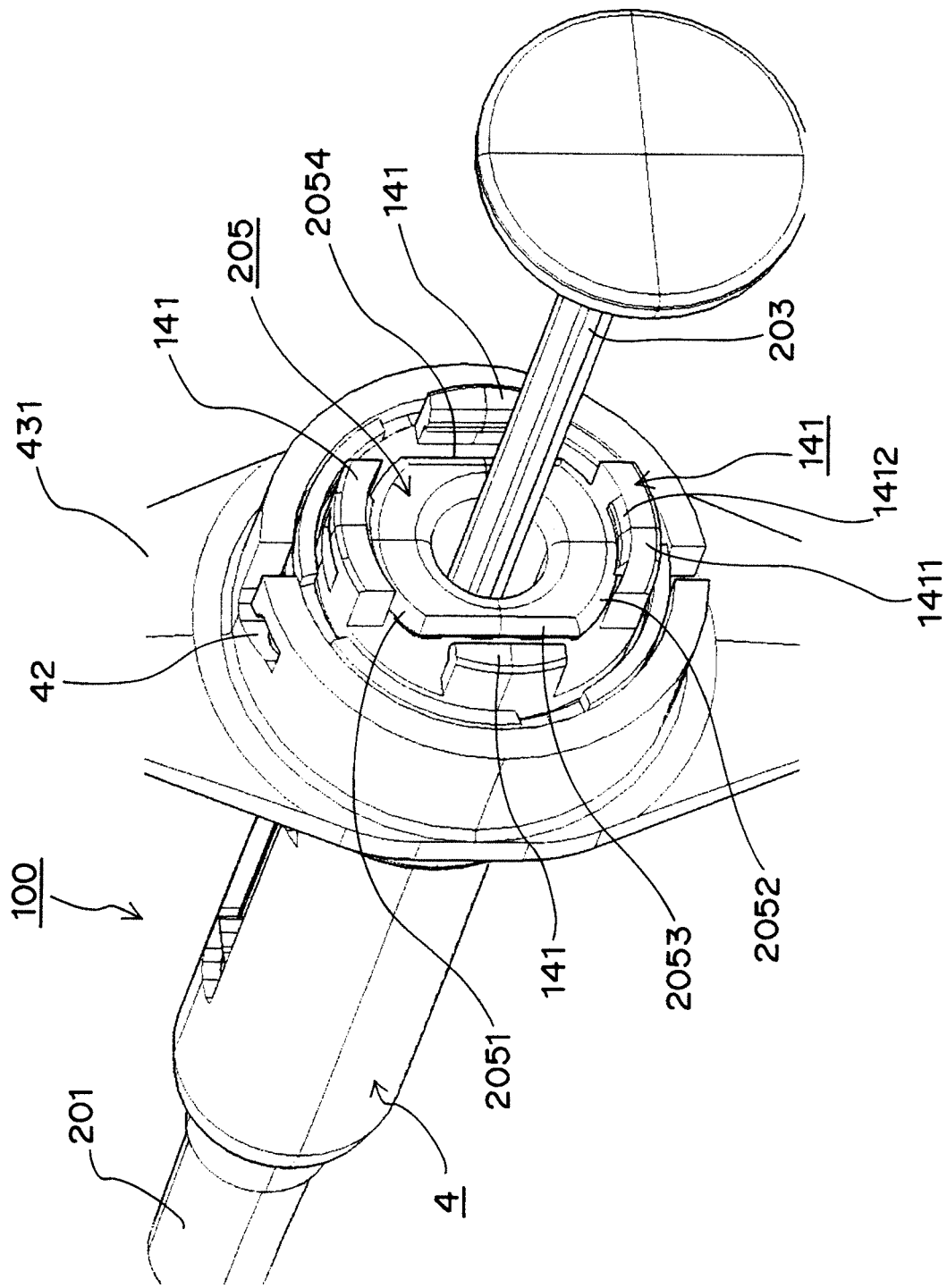
FIG. 33 is a perspective view showing a state in which the syringe is fixed to the protecting device.
Figure 34:
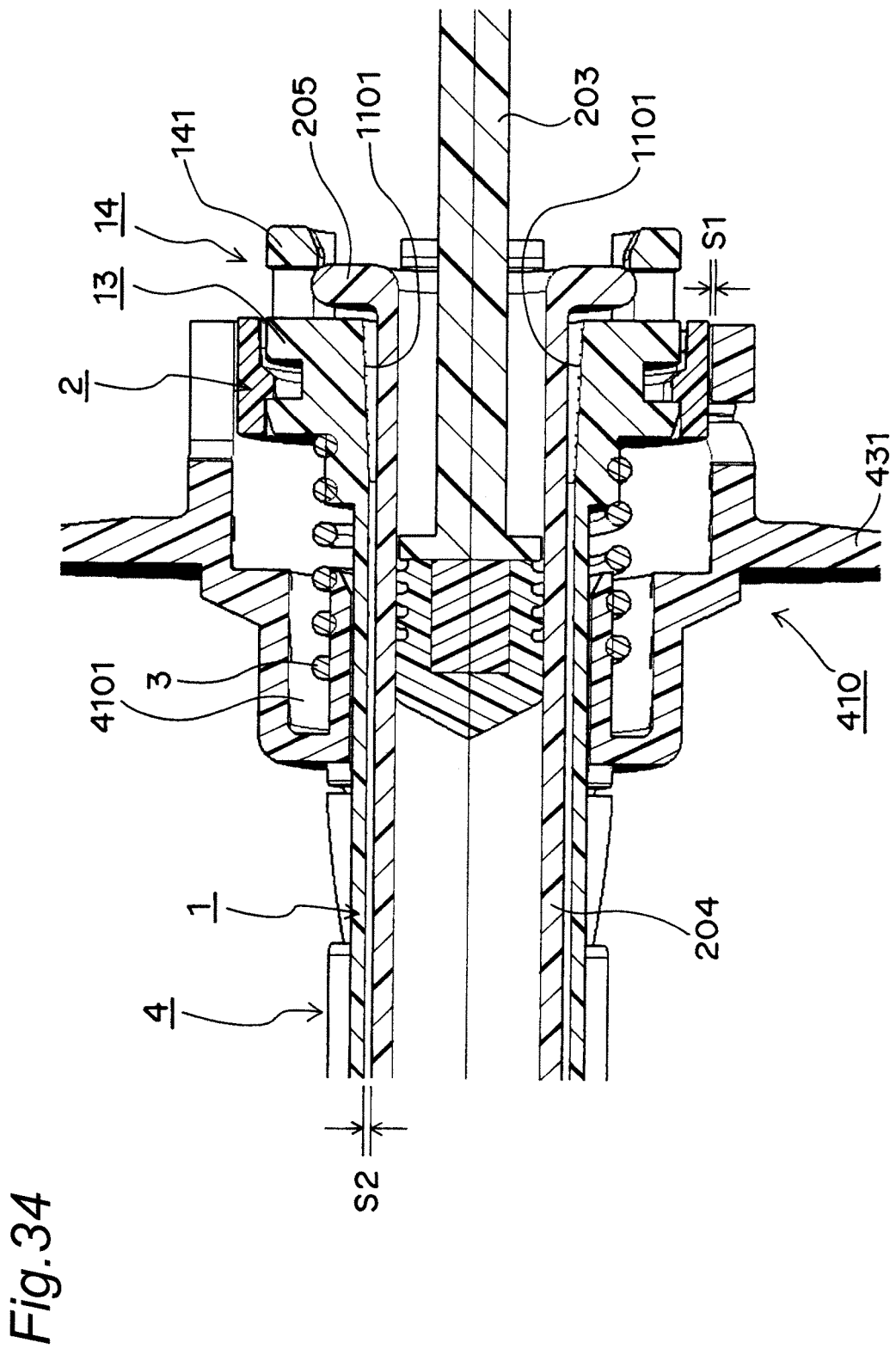
FIG. 34 is a side sectional view showing the state shown in FIG. 33.

As shown in FIG. 33, the syringe 200 is inserted into the inner cylinder 1 of the protecting device 100, and the flange 205 is mounted on the flange mounting section 14. FIG. 34 is a side sectional view showing the state shown in FIG. 33.

Figure 35:
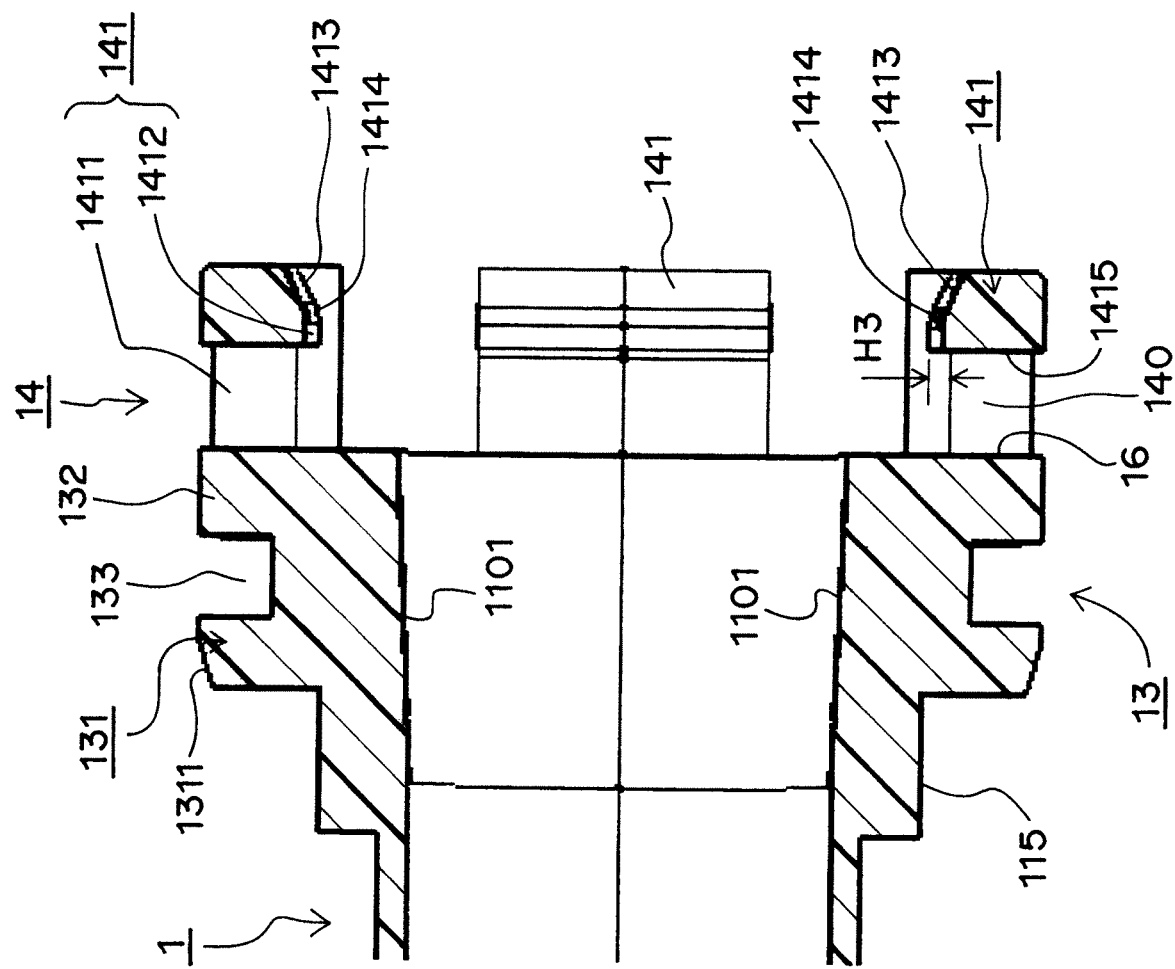
FIG. 35 is an enlarged side sectional view showing the pawl sections of a flange mounting section.

As shown in FIG. 35, each of the pawl sections 141 of the flange mounting section 14 is composed of a wall section 1411 extended rearward and a protruding section 1412 extended inward from the wall section 1411. A space 140 for accommodating the flange 205 is secured between the front faces 1415 of the protruding sections 1412 and the rear end face 16 of the inner cylinder 1. The flange 205 climbs over the protruding sections 1412 from behind and enters the space 140, thereby being held with the pawl sections 141 inside the space 140. The flange 205 has a nearly quadrangular shape in a rear view; the upper side 2051 and the lower side 2052 thereof are formed into an arc shape, and both the sides 2053 and 2054 thereof are formed into a linear shape. In other words, the flange 205 is an element generally referred to as "a cut flange". The wall sections 1411 of the pawl sections 141 are formed along the four sides of the flange 205. In other words, the wall sections 1411 of the upper and lower pawl sections 141 are formed into an arc shape, and the wall sections 1411 of the pawl sections 141 on both sides are formed into a linear shape. Hence, the flange 205 does not rotate inside the space 140. Furthermore, the flange 205 is held between the protruding sections 1412 and the rear end face 16 of the inner cylinder 1. Consequently, the flange 205 can be firmly secured to the flange mounting section 14.

Moreover, as shown in FIG. 35, a tapered face 1413 is formed rearward and outward at the tip end section of the protruding section 1412, and the front edge 1414 of the tapered face 1413 is rounded. Hence, the work for moving the flange 205 so that it climbs over the protruding sections 1412 from behind can be performed smoothly.

Furthermore, since the inner face of the large diameter section 110 of the inner cylinder 1 is formed into a tapered face 1101 so as to be slightly larger in diameter rearward, the inner face can smoothly guide the syringe 200 into the inner cylinder 1.

What's more, the inner cylinder 1 has an inside diameter so as to have a clearance S2 (see FIG. 34) with respect to the syringe body 204 of the syringe 200 having been inserted thereto. If the dimension of the clearance S2 is too small, it is difficult to insert the syringe body 204; if the dimension is too large, the syringe body 204 wobbles inside the inner cylinder 1 or the post-locking mechanism is likely to be released. Hence, the dimension of the clearance S2 has been set so as to be able to prevent these problems.

As described above, the protecting device 100 is mounted on the syringe 200.

[Use of the Syringe]

The syringe 200 on which the protecting device 100 is mounted has a state shown in FIG. 2. In this state, the operator holds the syringe 200 by putting two fingers on the side sections 431 of the flange section 43 from the front side as if handling a slightly larger syringe. Next, the operator removes the cap 201 to expose the syringe needle 202. The operator then sticks the syringe needle 202 in an injection site.

Each of the side sections 431 has a size enough to be pressed with a finger. Hence, the operator can stably operate the syringe 200 equipped with the protecting device 100.

Furthermore, the front end section of the outer cylinder 4 has a tapered face 46 (see FIG. 21) so as to become smaller in diameter toward the front. Hence, when the syringe 200 is oriented at the time of the sticking of the syringe needle 202, the front end section of the outer cylinder 4 is prevented from becoming an obstacle, whereby the injection angle of the syringe 200 can be made larger.

[Operation]

Next, the operation of the protecting device 100 will be described.

In a state in which the administration of a medicinal solution from the syringe 200 is completed by pressing the plunger rod 203, when the plunger rod 203 is further pressed forward together with the inner cylinder 1, the protruding section 22 positioned at the engaging section 423 of the through groove section 42 comes out forward from the engaging section 423, is further moved forward along the inclined section 422, and then reaches the front end of the straight section 421 as shown in FIG. 5.

Since the protruding section 22 has a tapered face 221 so as to be formed along the inclined section 422 in a plan view as shown in FIG. 16, the protruding section 22 moves smoothly along the inclined section 422. In addition, since a clearance S1 (see FIG. 34) is provided between the outer circumferential face of the ring 2 and the inner face of the large diameter section 410 of the outer cylinder 4, the ring 2 rotates smoothly. Hence, the protruding section 22 moves smoothly.

When the protruding section 22 reaches the front end of the straight section 421, the protruding section 22 can move rearward along the straight section 421. In other words, the pre-locking mechanism is released. As a result, as shown in FIG. 6, the spring 3 is released from its compressed state, and the inner cylinder 1 is pressed and moved rearward by the spring 3. Since the inner cylinder 1 holds the syringe 200, the syringe 200 is also moved rearward with respect to the outer cylinder 4.

If the protruding height H2 (see FIG. 18) of the protruding section 22 is too small, the protruding section 22 is hardly retained inside the engaging section 423; if the protruding height H2 is too large, the protruding section 22 becomes an obstacle, whereby the protruding height is set to a dimension not causing these problems.

When the inner cylinder 1 is moved rearward, the protruding sections 122 of the tongue sections 12 are moved rearward along the groove bodies 451 of the slide groove sections 45. In other words, the movement of the inner cylinder 1 is guided by the protruding sections 122. Hence, the inner cylinder 1 is moved stably. Furthermore, since the inner cylinder 1 is supported from the outside by the spring supporting section 44 of the large diameter section 410, the inner cylinder 1 is moved stably.

When the protruding sections 122 of the tongue sections 12 having been moved rearward engage with the engaging sections 452 of the slide groove sections 45, the movement of the inner cylinder 1 stops. The dimension of the slide groove section 45 in the front-rear direction is set to the distance along which the inner cylinder 1 is moved until the tip end of the syringe needle 202 is accommodated inside the outer cylinder 4. Hence, when the protruding section 122 engages with the engaging sections 452, the syringe needle 202 is stored inside the inner space 413 of the outer cylinder 4.

Since the protruding sections 122 having engaged with the engaging sections 452 of the slide groove sections 45 cannot move in the front-rear direction, the inner cylinder 1 having moved rearward is fixed to the outer cylinder 4. In other words, with the post-locking mechanism composed of the tongue sections 12 and the slide groove sections 45, since the protruding sections 122 of the tongue sections 12 can be firmly held by the engaging sections 452 of the slide groove sections 45, the inner cylinder 1 having been operated can be firmly fixed to the outer cylinder 4; hence, the storage state of the syringe needle 202 can be maintained firmly, and the syringe needle 202 can be prevented from being exposed, for example, when the protecting device 100 is stored or discarded after the operation of the protecting device 100, whereby needle sticking accidents can be prevented.

Figure 36:
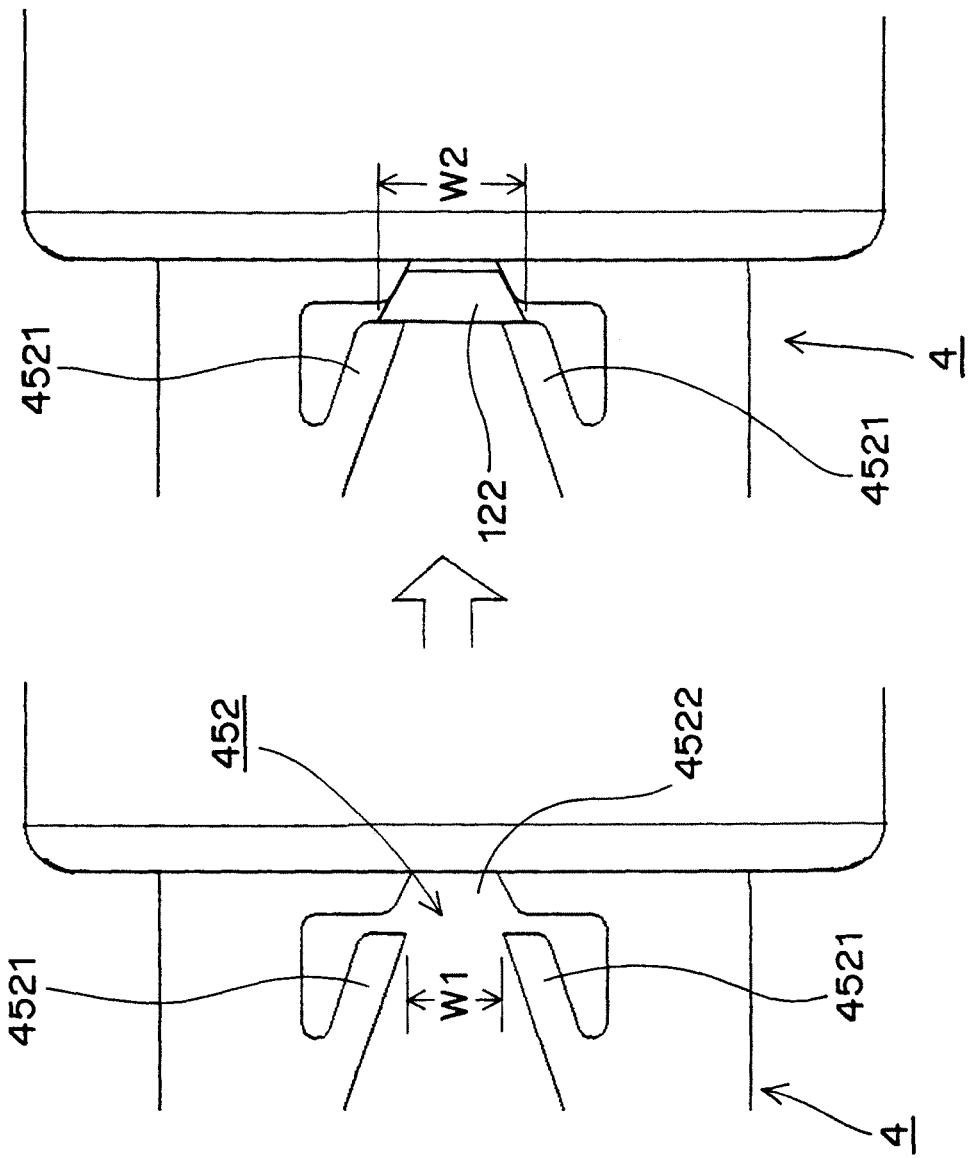
FIG. 36 is an enlarged plan view showing a state in which the protruding section of a tongue section is engaged with the engaging space of a slide groove section.

Moreover, as shown in FIG. 36, since the engaging space 4522 is formed into a trapezoidal shape that is narrower rearward in a plan view and since the protruding section 122 is formed into a trapezoidal shape so as to be fitted into the engaging space 4522 in a plan view, the protruding section 122 is fitted into the engaging space 4522. What's more, the distance W1 between the tip ends of the two reverse movement preventing pieces 4521 is smaller than the width W2 of the front section of the protruding section 122. Hence, the protruding section 122 is firmly fixed so as not to be movable inside the engaging space 4522. Consequently, the post-locking mechanism operates firmly.

If the protruding height H1 (see FIG. 13) of the protruding section 122 is too small, the protruding section 122 is hardly retained inside the engaging section 452; if the protruding height H1 is too large, the protruding section 122 becomes an obstacle when the inner cylinder 1 is inserted into the outer cylinder 4, whereby the protruding height is set to a dimension not causing these problems.

Furthermore, the energizing force of the spring 3 is set as described below.

(a) When the flange 205 is mounted on the flange mounting section 14, a forward pressing force is applied to the inner cylinder 1 so that the flange 205 climbs over the protruding sections 1412. In this case, there is a risk that the pre-locking mechanism may be released. However, since the energizing force of the spring 3 has been set so as to be larger than the pressing force, the pre-locking mechanism is not released. In other words, no malfunction occurs. More specifically, the energizing force of the spring 3 has been set so as to be larger than the pressing force by 50 to 400%, preferably, 100 to 300%.

(b) When the plunger rod 203 is pressed to administer a medical solution, a sliding resistance occurs at the plunger rod 203 with respect to the syringe body 204. In this case, a forward pressing force is applied to the inner cylinder 1, and there is a risk that the pre-locking mechanism may be released. However, since the energizing force of the spring 3 has been set so as to be larger than the sliding resistance, the pre-locking mechanism is not released. In other words, no malfunction occurs. More specifically, the energizing force of the spring 3 has been set so as to be larger than the sliding resistance by 100 to 600%, preferably, 100 to 300%.

(c) Even if the spring 3 is released from its compressed state, in the case that the protruding section 122 does not reach the engaging section 452, the syringe needle 202 is not stored completely, and the inner cylinder 1 having been moved rearward is not fixed to the outer cylinder 4. In other words, the protecting device 100 cannot exhibit its protection function. However, the energizing force of the spring 3 has been set so as to be able to move the inner cylinder 1 to the position where the syringe needle 202 is stored into the outer cylinder 4, that is, to the position where the protruding sections 122 engages with the engaging sections 452. Hence, the protecting device 100 can sufficiently exhibit its protection function.

[Modifications]

The following modifications can be adopted for the respective elements.

(1) The number of the tongue sections 12 is not limited to two, but the number may be one or three or more.

(2) The tongue section 12, two or more in number, may be provided at positions not opposed to one another in the circumferential direction.

(3) The protruding section 122 of the tongue section 12 may have an elliptical shape, a semicircular shape, a triangular shape or a rectangular shape in a plan view.

(4) The number of the protruding sections 22 of the ring 2 is not limited to two, but the number may be one or three or more.

(5) The protruding sections 22 of the ring 2, two or more in number, may be provided at positions not opposed to one another in the circumferential direction.

(6) The protruding sections 22 of the ring 2 may have an elliptical shape or a rectangular shape in a plan view.

(7) The protruding sections 22 of the ring 2 may be colored. This can improve the visibility of the pre-locking mechanism.

Figure 37:
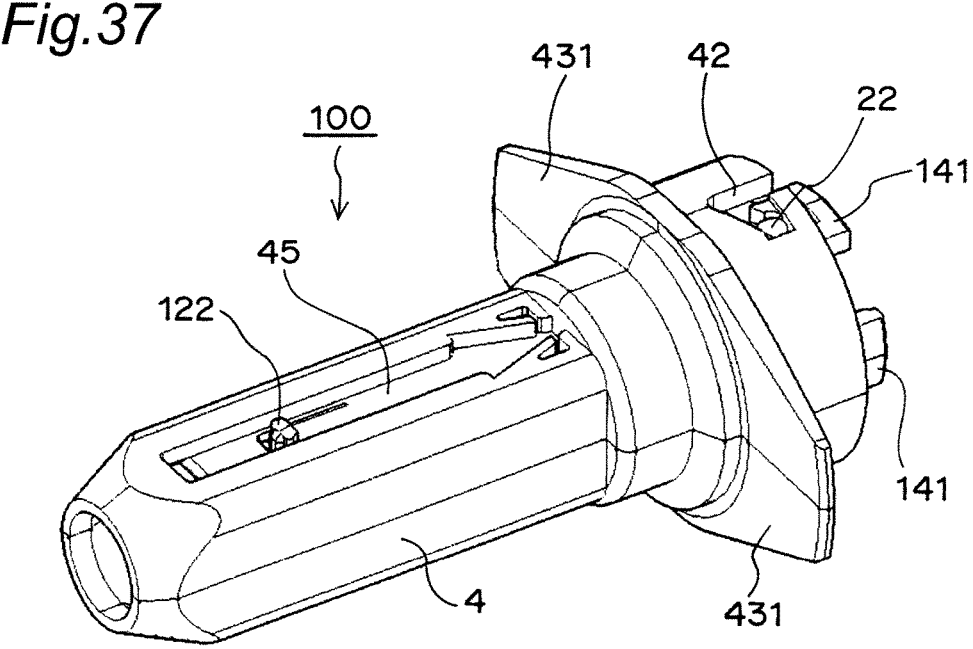
FIG. 37 is a perspective view showing a syringe protecting device in which each of the outer cylinder and the inner cylinder has a quadrangular shape in cross section.
Figure 38:
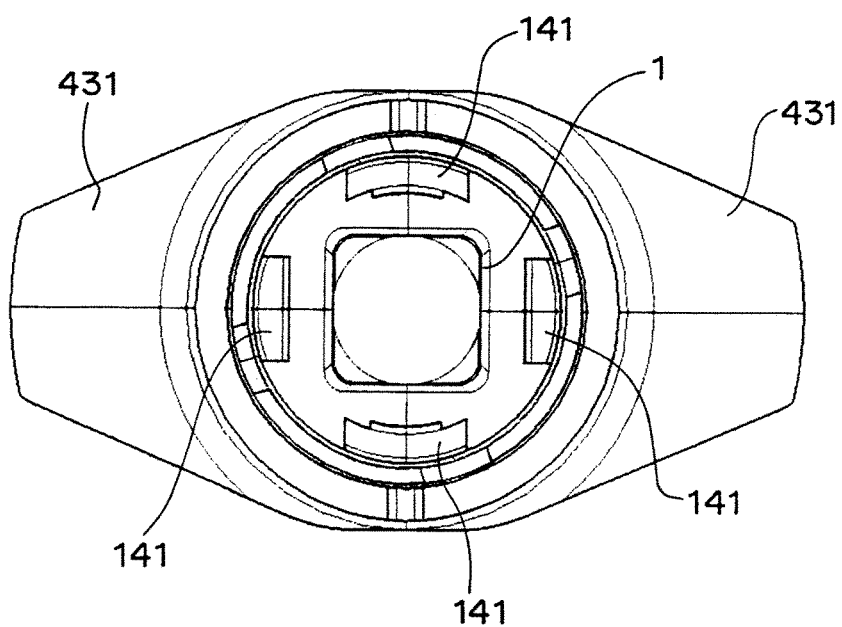
FIG. 38 is a rear view showing the syringe protecting device shown in FIG. 37.

(8) As shown in FIG. 37, each of the inner cylinder 1 and the outer cylinder 4 may be a cylinder having a quadrangular shape in cross section. In this case, labels and the like can be attached easily to the surface of the outer cylinder 4. FIG. 38 is a rear view showing the protecting device 100 shown in FIG. 37.

(9) The number and the positions in the circumferential direction of the through groove sections 42 may merely correspond to the number and the positions in the circumferential direction of the protruding sections 22.

(10) The number and the positions in the circumferential direction of the slide groove sections 45 may merely correspond to the number and the positions in the circumferential direction of the tongue sections 12.

(11) The spring supporting section 44 is not required to be continuous in the circumferential direction; for example, the spring supporting section may be composed of a plurality of rods provided at appropriate intervals in the circumferential direction.

(12) The flange 205 of the syringe 200 may have a circular shape (generally referred to as "a round flange") in a rear view.

[Specific Dimensions]

Specific dimensions of the respective sections in the protecting device 100 for use in the syringe 200 having a capacity of 1 ml are, for example, as described below:

The length L1 of the tongue piece 121 in the front-rear direction (see FIG. 12): 3 to 12 mm The protruding height H1 of the protruding section 122 (see FIG. 13): 0.5 to 2.5 mm The protruding height H2 of the protruding section 22 (see FIG. 18): 0.5 to 3 mm The clearance S2 (see FIG. 34): 0.1 to 0.6 mm The protruding dimension H3 of the protruding section 1412 (see FIG. 35): 0.2 to 0.7 mm

INDUSTRIAL APPLICABILITY

The syringe protecting device according to the present invention can allow a syringe to be used safely and effectively while preventing malfunction, thereby being high in industrial utility value.

REFERENCE SIGNS LIST

1 inner cylinder
12 tongue section
122 protruding section
2 ring
22 protruding section
3 spring
4 outer cylinder
42 through groove section
421 straight section
422 inclined section
423 engaging section
44 spring supporting section
45 slide groove section
452 engaging section
4521 reverse movement preventing piece
100 syringe protecting device
200 syringe
202 syringe needle
203 plunger rod
204 syringe body

The invention claimed is:

1. A syringe protecting device, when mounted on a syringe and used, operating so as to store a syringe needle after the administration of a medical solution, comprising:
an outer cylinder having a front end opening and a rear end opening,
an inner cylinder, having a front end opening and a rear end opening and inserted into the outer cylinder, to which the syringe can be inserted and fixed, and
a spring provided in a circumferential space between an inner face of a rear section of the outer cylinder and an outer face of a rear section of the inner cylinder in a compressed state in the front-rear direction so that the inner cylinder is energized rearward with respect to the outer cylinder, wherein when the spring is released from the compressed state, the inner cylinder is moved rearward with respect to the outer cylinder so that the syringe needle is stored inside the outer cylinder, the syringe protecting device further comprising:

a releasable pre-locking mechanism for fixing the inner cylinder to the outer cylinder while maintaining the spring in a compressed state in the front-rear direction, wherein the pre-locking mechanism comprises:

a ring, different from the inner cylinder and the outer cylinder, being fitted on the rear section of the inner cylinder so as to be slidable in the circumferential direction and so as not to be movable in the front-rear direction, and through groove sections formed in the rear section of the outer cylinder, wherein the ring has one or more outward protruding sections in the circumferential direction, the outward protruding sections are engaged with the engaging sections of the through groove sections, and the through groove section comprises a straight section being open at the rear end edge thereof and extended in the front-rear direction, an inclined section extended obliquely rearward from the front end of the straight section, and the engaging section extended rearward linearly from the rear end of the inclined section, wherein in the case that the inner cylinder is pressed so as to further compress the spring, the ring is rotated in the circumferential direction with respect to the inner cylinder and the outer cylinder, the protruding sections come out from the engaging sections, pass through the inclined sections and enter the straight sections, whereby the pre-locking mechanism is released, and when the pre-locking mechanism is released, the inner cylinder is moved rearward with respect to the outer cylinder by the spring by the distance along which the syringe needle is moved and stored in the outer cylinder.

2. The syringe protecting device according to claim 1, further comprising a post-locking mechanism for fixing the inner cylinder having been moved rearward to the outer cylinder, wherein the post-locking mechanism comprises:

at least one slide groove section formed so as to be extended in the front-rear direction from the central section to the front section of the outer cylinder and at least one tongue section formed on a peripheral wall of the front section of the inner cylinder, wherein the at least one tongue section is extended in the front-rear direction, is elasticity deformable inward and outward while the rear end thereof is used as a base end and has an outwardly protruding section at the front end section thereof, and the at least one slide groove section is formed so that, in the state in which the inner cylinder is fixed to the outer cylinder before the inner cylinder is moved rearward, the protruding section of the tongue section is positioned inside the slide groove section and so that, in the state in which the inner cylinder has been moved rearward, the outwardly protruding section of the tongue section is unmovably engaged with an engaging section of a rear end of the at least one slide groove section.

3. The syringe protecting device according to claim 2, wherein the engaging section of the at least one slide groove section of the post-locking mechanism is equipped with a reverse movement preventing piece allowing the outwardly protruding section of the at least one tongue section to move rearward but preventing the outwardly protruding section from moving forward.

4. The syringe protecting device according to claim 1, wherein the spring being compressed in the front-rear direction has been set so as to have an energizing force that is larger than a sliding resistance of a plunger rod of the syringe with respect to the syringe body of the syringe and also larger than the pressing force for fixing the syringe to the inner cylinder and that is capable of moving the inner cylinder to the position where the syringe needle is stored inside the outer cylinder.

5. The syringe protecting device according to claim 1, wherein the outward protruding sections of the ring of the pre-locking mechanism are formed at two positions opposed to each other in the circumferential direction, and the through groove sections of the pre-locking mechanism are formed at two positions opposed to each other in the circumferential direction of the rear section of the outer cylinder.

6. The syringe protecting device according to claim 2, wherein the at least one slide groove sections of the post-locking mechanism are formed at two positions opposed to each other in the circumferential direction of the outer cylinder, and the at least one tongue sections of the post-locking mechanism are formed at two positions opposed to each other in the circumferential direction of the inner cylinder.

7. The syringe protecting device according to claim 3, wherein the at least one slide groove sections of the post-locking mechanism are formed at two positions opposed to each other in the circumferential direction of the outer cylinder, and the at least one tongue sections of the post-locking mechanism are formed at two positions opposed to each other in the circumferential direction of the inner cylinder.

8. The syringe protecting device according to claim 1, wherein the rear section of the outer cylinder has a spring supporting section for supporting the front section of the spring from the inside in the circumferential space.

9. The syringe protecting device according to claim 1, wherein the outer cylinder and the inner cylinder are made of transparent resin.

10. The syringe protecting device according to claim 1, wherein each of the cylindrical bodies of the outer cylinder and the inner cylinder has a circular shape or a quadrangular shape in cross section.

11. The syringe protecting device according to claim 1, wherein a space is provided between the outer circumferential face of the ring and the inner face of the rear section of the outer cylinder.

12. A safe syringe wherein the syringe protecting device according to claim 1 is mounted on a syringe equipped with a syringe needle, a syringe body storing a medical solution and a plunger rod for pushing out the medical solution.

13. A safe syringe wherein the syringe protecting device according to claim 2 is mounted on a syringe equipped with a syringe needle, a syringe body storing a medical solution and a plunger rod for pushing out the medical solution.

\* \* \* \* \*